United States Patent
Takata et al.

(10) Patent No.: US 9,086,402 B2
(45) Date of Patent: Jul. 21, 2015

(54) SAMPLE ANALYZER

(75) Inventors: Rumi Takata, Kobe (JP); Yousuke Tanaka, Kobe (JP); Noriyuki Narisada, Akasha (JP); Junya Inoue, Kobe (JP)

(73) Assignee: Sysmex Corporation, Hyogo (JP)

( * ) Notice: Subject to any disclaimer, the term of this patent is extended or adjusted under 35 U.S.C. 154(b) by 1124 days.

(21) Appl. No.: 12/986,887

(22) Filed: Jan. 7, 2011

(65) Prior Publication Data

US 2011/0169837 A1 Jul. 14, 2011

(30) Foreign Application Priority Data

Jan. 8, 2010 (JP) .................................. 2010-003211
Jan. 8, 2010 (JP) .................................. 2010-003215

(51) Int. Cl.
*G06T 11/20* (2006.01)
*G09G 5/22* (2006.01)
*G01N 33/493* (2006.01)
*G01N 15/14* (2006.01)
*G01N 15/00* (2006.01)

(52) U.S. Cl.
CPC .............. *G01N 33/493* (2013.01); *G01N 15/14* (2013.01); *G01N 15/1429* (2013.01); *G01N 2015/008* (2013.01); *G01N 2015/1493* (2013.01)

(58) Field of Classification Search
USPC ......................................................... 600/300
See application file for complete search history.

(56) References Cited

U.S. PATENT DOCUMENTS

| 7,582,473 B2 | 9/2009 | Kawashima |
| 2004/0219627 A1 | 11/2004 | Kawashima |
| 2005/0042744 A1 | 2/2005 | Kawashima |
| 2005/0079569 A1 | 4/2005 | Kawashima |

FOREIGN PATENT DOCUMENTS

| CN | 101173888 A | 5/2008 |
| CN | 101245368 A | 8/2008 |
| CN | 101545846 A | 9/2009 |
| CN | 101545863 A | 9/2009 |
| EP | 0 949 498 A2 | 10/1999 |
| EP | 1 857 805 A2 | 11/2007 |
| JP | 5-34263 A | 2/1993 |
| JP | 9-229926 A | 9/1997 |
| JP | 11-295207 A | 10/1999 |
| JP | 2001-149091 A | 6/2001 |
| JP | 2002-202302 A | 7/2002 |

(Continued)

OTHER PUBLICATIONS

G.R.E. Naylor, J Med Microbiol, Feb. 1984, vol. 17 No. 1, 31-36.*

*Primary Examiner* — David Zarka
*Assistant Examiner* — Robert Craddock
(74) *Attorney, Agent, or Firm* — Sughrue Mion, PLLC

(57) ABSTRACT

A sample analyzer comprising: a light source for emitting light to particles contained in a measurement sample which is prepared from a reagent and a urine sample collected from a subject; a detector for detecting scattered light and fluorescence which are generated from the particles in the measurement sample; a display; and a controller, wherein the controller executes operations comprising: obtaining particle data based on the scattered light and the fluorescence which are detected from the particles by the detector; and controlling, when the particle data satisfies a predetermined condition, the display to display information indicating a possibility that the subject is infected with an uncomplicated urinary tract infection is disclosed.

10 Claims, 17 Drawing Sheets

(56) References Cited

FOREIGN PATENT DOCUMENTS

| JP | 2004-125787 A | 4/2004 |
| JP | 2004-305173 A | 11/2004 |
| JP | 2006-17497 A | 1/2006 |
| JP | 2007-78508 A | 3/2007 |
| JP | 2007-309728 A | 11/2007 |
| JP | 2007-309765 A | 11/2007 |

* cited by examiner

F I G. 1
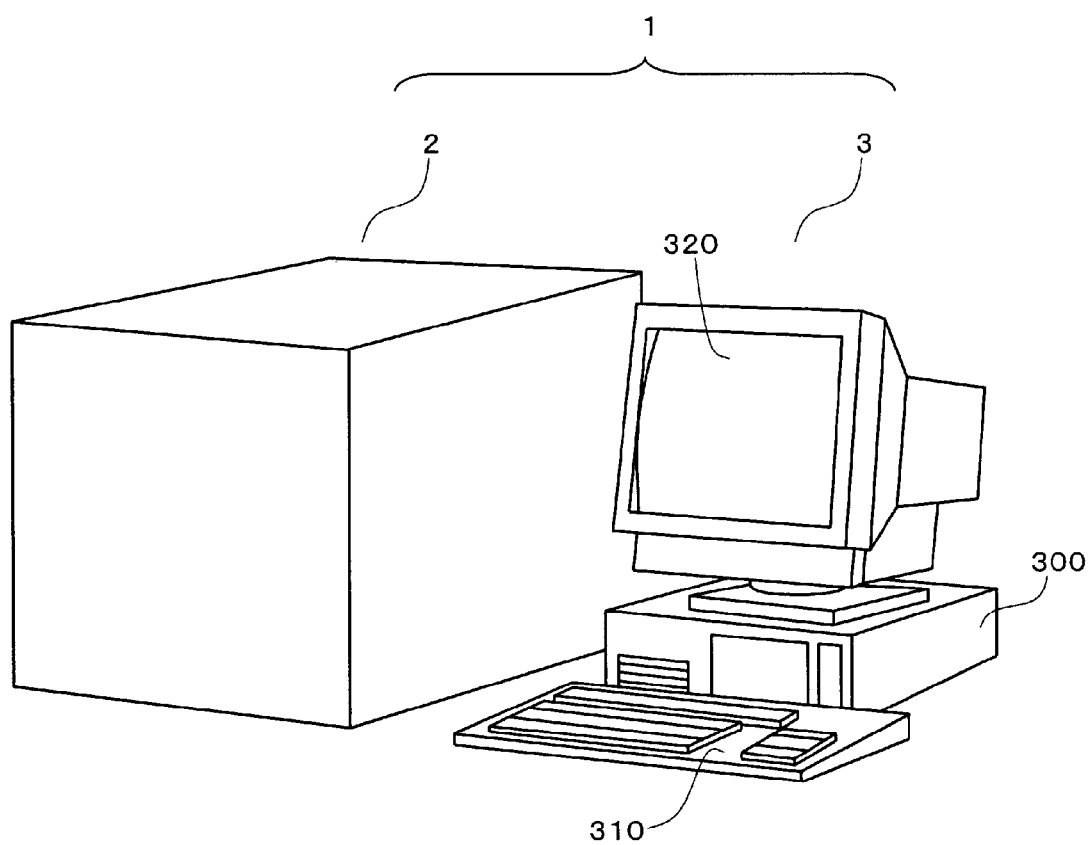

FIG. 5
(a) CONTROL BY CPU 204
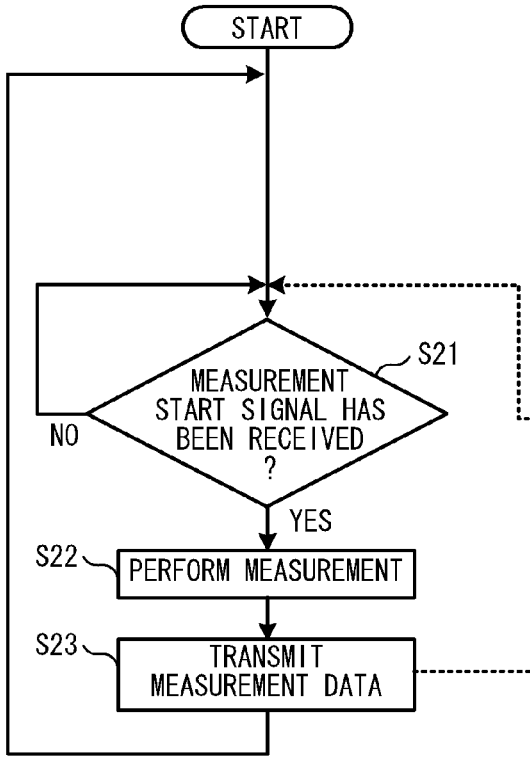
(b) CONTROL BY CPU 301
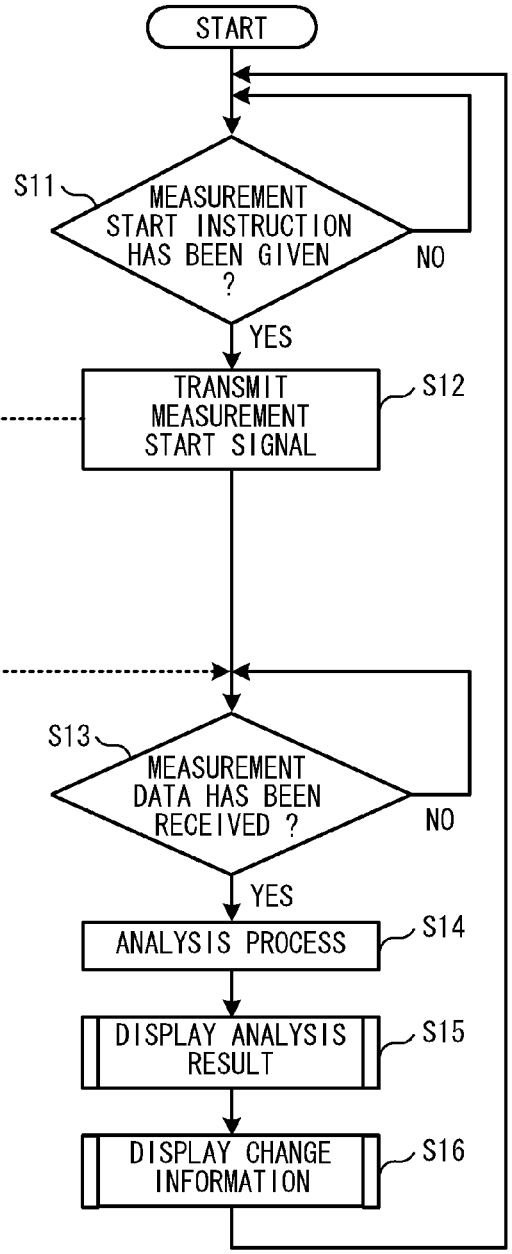

FIG. 11

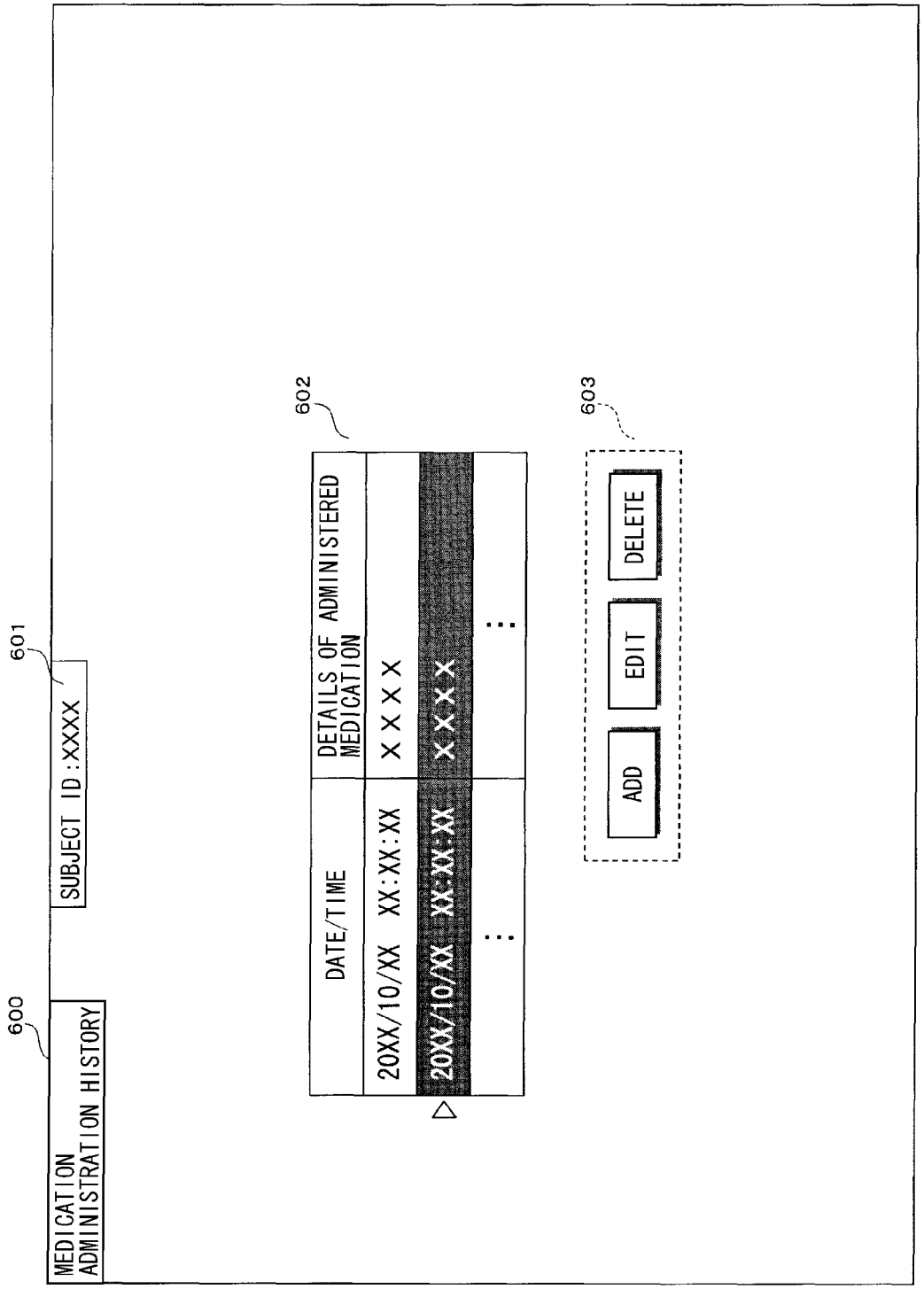

SAMPLE ANALYZER

RELATED APPLICATIONS

This application claims priority under 35 U.S.C. §119 to Japanese Patent Application No. 2010-3211 filed on Jan. 8, 2010 and Japanese Patent Application No. 2010-3215 filed on Jan. 8, 2010, the entire contents of which are hereby incorporated by reference.

FIELD OF THE INVENTION

The present invention relates to a sample analyzer for analyzing a sample by irradiating, with light, a measurement sample which is prepared from a sample and a reagent.

BACKGROUND

Currently, detection of bacteria is performed in clinical laboratory tests and the like. Detection of bacteria can be performed, for example, by a method in which a sample is cultured and colonies formed in the sample are visually examined. This method allows the types and number of bacteria contained in the sample to be identified. However, it takes a few days for the colonies to form in the cultured sample. Thus, this examination method has a problem in that it lacks promptness.

In relation to this problem, U.S. patent application publication 20040219627 discloses a bacteria determination method that uses a scattergram. In this method, a scattergram is created, in which size information and fluorescence information about bacteria in a sample are used as parameters. Then, the state of distribution of bacteria in the scattergram is analyzed. Based on the analysis results, it is determined whether the type of bacteria in the sample is a bacillus or a coccus.

However, with the method disclosed by U.S. patent application publication 20040219627, if multiple types of bacteria are contained in a sample, it is difficult to determine the respective types of bacteria in the sample. Therefore, even if the method of U.S. patent application publication 20040219627 is used in analysis of a urine sample, it is difficult for the user of the method to determine whether a urinary tract infection indicated by the urine sample is a complicated urinary tract infection or uncomplicated urinary tract infection.

Moreover, although the method of U.S. patent application publication 20040219627 determines a bacterial type, the method is unable to provide other information to the user. In terms of treatment and diagnosis, if, for example, the user is promptly informed that the types of bacteria in a sample collected from a subject have changed as compared to another sample previously collected from the same subject, then the user can properly know the progression of a disease of the subject as well as the effectiveness of medication and treatment of the disease that have been performed. Such information allows the user to take appropriate measures to address the disease of the subject.

SUMMARY OF THE INVENTION

A first aspect of the present invention is a sample analyzer comprising: a light source for emitting light to particles contained in a measurement sample which is prepared from a reagent and a urine sample collected from a subject; a detector for detecting scattered light and fluorescence which are generated from the particles in the measurement sample; a display; and a controller, wherein the controller executes operations comprising: obtaining particle data based on the scattered light and the fluorescence which are detected from the particles by the detector; and controlling, when the particle data satisfies a predetermined condition, the display to display information indicating a possibility that the subject is infected with an uncomplicated urinary tract infection.

A second aspect of the present invention is a sample analyzer comprising: a light source for emitting light to particles contained in a measurement sample which is prepared from a sample and a reagent; a detector for detecting scattered light and fluorescence which are generated from the particles in the measurement sample; a display; and a controller, wherein the controller executes operations comprising: obtaining, for each particle in the measurement sample, particle data which comprise numerical values obtained from the scattered light and the fluorescence detected from the particle; determining one of a plurality of numerical ranges to which each of the particle data belongs; generating a histogram that indicates, for each numerical value range, the number of particles belonging thereto; and controlling the display to display the histogram.

A third aspect of the present invention is a sample analyzer comprising: a light source for emitting light to a measurement sample which is prepared from a reagent and a sample collected from a subject; a detector for detecting scattered light and fluorescence which are generated from the measurement sample; a memory; a display; and a controller, wherein the controller executes operations comprising: obtaining a measurement result based on the scattered light and the fluorescence; storing the measurement result in the memory; determining, based on the measurement result of the subject that has most recently been obtained and the measurement result of the subject that has previously been stored in the memory, whether a type of bacteria that the subject is suspected to be infected with has changed; and controlling, when the type of bacteria has changed, the display to display information indicating that the type of bacteria has changed.

BRIEF DESCRIPTION OF THE DRAWINGS

FIG. 1 shows an external configuration of a urine sample analyzer according to an embodiment of the present invention;

FIG. 5 shows flowcharts showing a measurement process of measuring a sample and an analysis process of analyzing the sample, according to the embodiment;

FIG. 11 shows an example of a chronological display screen displayed by the display unit of the information processing apparatus according to the embodiment;

FIG. 12 shows an example of a medication administration history screen displayed by the display unit of the information processing apparatus according to the embodiment;

DESCRIPTION OF THE PREFERRED EMBODIMENTS

In an embodiment described below, the present invention is applied to a urine sample analyzer for performing measurement on bacteria contained in a urine sample and determining based on the measurement results the types of bacteria in the urine sample.

Hereinafter, the urine sample analyzer according to the present embodiment will be described with reference to the drawings.

FIG. 1 shows an external configuration of a urine sample analyzer 1 according to the present embodiment.

The urine sample analyzer 1 includes a measurement apparatus 2 and an information processing apparatus 3. The measurement apparatus 2 optically measures bacteria contained in a urine sample by means of a flow cytometer. The information processing apparatus 3 analyzes the results of the measurement performed by the measurement apparatus 2, and displays the analysis results on a display unit 320.

Figure 2:
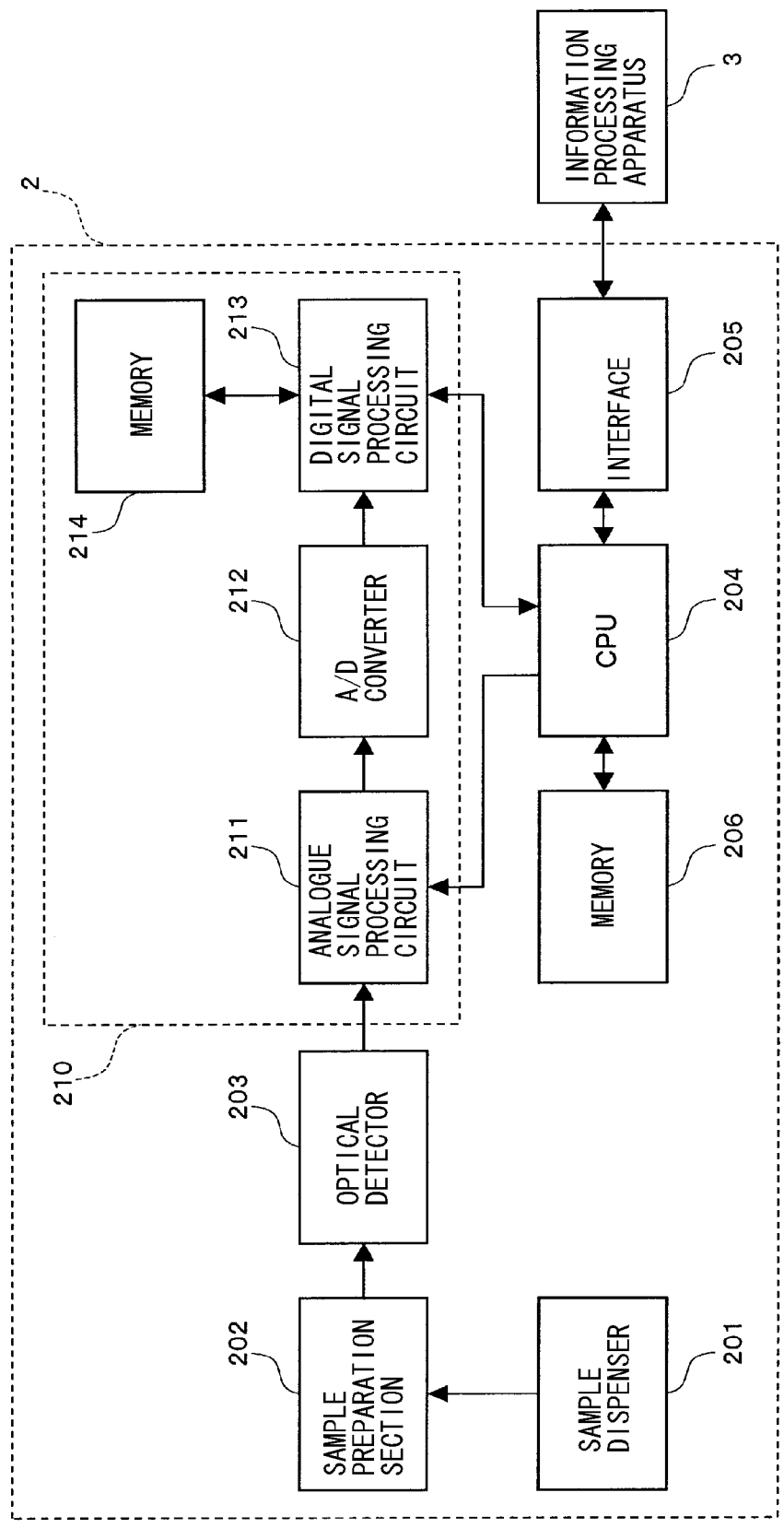
FIG. 2 shows a configuration of a measurement apparatus according to the embodiment.

FIG. 2 shows a configuration of the measurement apparatus 2.

The measurement apparatus 2 includes a sample dispenser 201, a sample preparation section 202, an optical detector 203, a signal processing circuit 210, a CPU 204, a communication interface 205, and a memory 206. The signal processing circuit 210 includes an analogue signal processing circuit 211, an A/D converter 212, a digital signal processing circuit 213, and a memory 214.

The sample dispenser 201 includes a pipette and a pump (not shown). When the pump is driven, a predetermined amount of sample (urine) is aspirated into the pipette, and then the sample that has been aspirated into the pipette is discharged. By means of the pipette and the pump, the sample dispenser 201 supplies the sample preparation section 202 with the predetermined amount of sample that the sample dispenser 201 has aspirated from a sample container.

The sample preparation section 202 includes a reagent container, a mixing container, and a pump (not shown). In the mixing container, the sample supplied from the sample dispenser 201 is mixed with a diluent solution and a staining solution that are supplied from the reagent container, and thereby a measurement sample is prepared. The measurement sample prepared in the mixing container is supplied by the pump to a sheath flow cell 203c (see FIG. 3) of the optical detector 203, together with a sheath liquid.

The optical detector 203 emits laser light to the measurement sample, and outputs electrical signals to the analogue signal processing circuit 211, which electrical signals are based on forward scattered light, side fluorescence, and side scattered light which are generated when the measurement sample is irradiated with the laser light. In accordance with an instruction from the CPU 204, the analogue signal processing circuit 211 amplifies the electrical signals outputted from the optical detector 203, and outputs the amplified electrical signals to the A/D converter 212.

The A/D converter 212 converts the electrical signals amplified by the analogue signal processing circuit 211 into digital signals, and outputs the digital signals to the digital signal processing circuit 213. In accordance with an instruction from the CPU 204, the digital signal processing circuit 213 performs predetermined waveform processing on the digital signals outputted from the A/D converter 212, and the digital signals on which the waveform processing has been performed are stored in the memory 214. Here, the digital signals stored in the memory 214 include signals that are based on pulse signals of forward scattered light and side fluorescence which are generated each time a bacterium passes through the sheath flow cell 203c.

The CPU 204 controls the analogue signal processing circuit 211 and the digital signal processing circuit 213. Also, the CPU 204 obtains, from the digital signals stored in the memory 214, the magnitude of each of the pulse signals of the forward scattered light and the side fluorescence. Here, the magnitude of a pulse signal of forward scattered light indicates the intensity of the forward scattered light, which is generated when a bacterium passes through the sheath flow cell 203c. Similarly, the magnitude of a pulse signal of side fluorescence indicates the intensity of the side fluorescence, which is generated when a bacterium passes through the sheath flow cell 203c. Here, the magnitude of the pulse signal of the forward scattered light represents the size of the bacterium, and the magnitude of the pulse signal of the side fluorescence represents the degree of staining of the nucleic acid of the bacterium.

After obtaining the magnitudes of the respective pulse signals of the forward scattered light and the side fluorescence, the CPU 204 generates, based on the magnitudes of the respective pulse signals, data cluster that indicates a forward scattered light intensity and a side fluorescence intensity for each of the bacteria that have passed through the sheath flow cell 203c (hereinafter, the data cluster is referred to as "measurement data"). The CPU 204 outputs the measurement data to the communication interface 205. Further, the CPU 204 receives control signals from the information processing apparatus 3 via the communication interface 205, and drives the respective components of the measurement apparatus 2 in accordance with the control signals.

The communication interface 205 transmits to the information processing apparatus 3 the measurement data outputted from the CPU 204, and receives the control signals outputted from the information processing apparatus 3. The memory 206 is used as a work area for the CPU 204.

Figure 3:
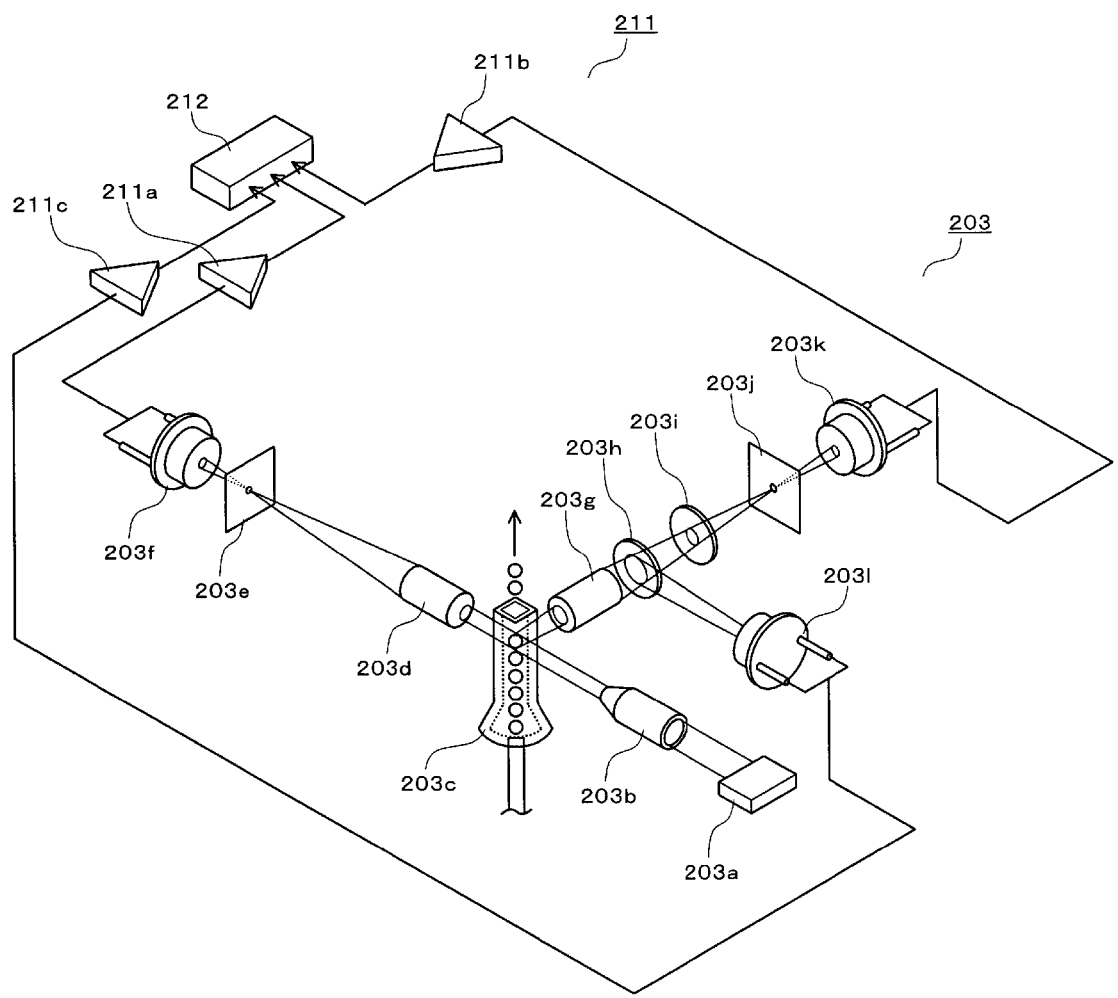
FIG. 3 is a schematic diagram showing configurations of an optical detector and an analogue signal processing circuit according to the embodiment.

FIG. 3 is a schematic diagram showing configurations of the optical detector 203 and the analogue signal processing circuit 211 of the measurement apparatus 2.

The optical detector 203 includes a light emitter 203a, an irradiation lens unit 203b, the sheath flow cell 203c, a condenser lens 203d, a pinhole plate 203e, a PD (photodiode) 203f, a condenser lens 203g, a dichroic mirror 203h, an optical filter 203i, a pinhole plate 203j, a PMT (photomultiplier tube) 203k, and a PD (photodiode) 203l. The analogue signal processing circuit 211 includes amplifiers 211a, 211b, and 211c.

Laser light emitted from the light emitter 203a is converted by the irradiation lens unit 203b into parallel light, and a sample flow containing the measurement sample is irradiated with the parallel light when passing through the sheath flow cell 203c. Note that the measurement sample passing through the sheath flow cell 203c is a mixture of a sample (a urine sample) to be measured and the aforementioned diluent solution and staining solution.

The condenser lens 203d is disposed in the path of the laser light emitted from the light emitter 203a. The forward scattered light, which is generated at the sheath flow cell 203c, is converged by the condenser lens 203d, and passes through the pinhole plate 203e, before being received by the PD 203f.

The condenser lens 203g is disposed in a path that intersects the path of the laser light emitted from the light emitter 203a. The side fluorescence and the side scattered light, which are generated at the sheath flow cell 203c, are converged by the condenser lens 203g and fall on the dichroic mirror 203h. The dichroic mirror 203h separates the side fluorescence and the side scattered light. The side fluorescence separated by the dichroic mirror 203h passes through the optical filter 203i and the pinhole plate 203j, and is then received by the PMT 203k. The side scattered light separated by the dichroic mirror 203h is received by the PD 203l.

The PD 203f, the PMT 203k, and the PD 203l output electrical signals based on the received forward scattered light, side fluorescence, and side scattered light, respectively. The amplifiers 211a, 211b, and 211c amplify the electrical signals outputted from the PD 203f, the PMT 203k, and the PD 203l, respectively, and output the resultant signals to the A/D converter 212. Note that the amplifiers 211a, 211b, and 211c are included in the analogue signal processing circuit 211 shown in FIG. 2.

Figure 4:
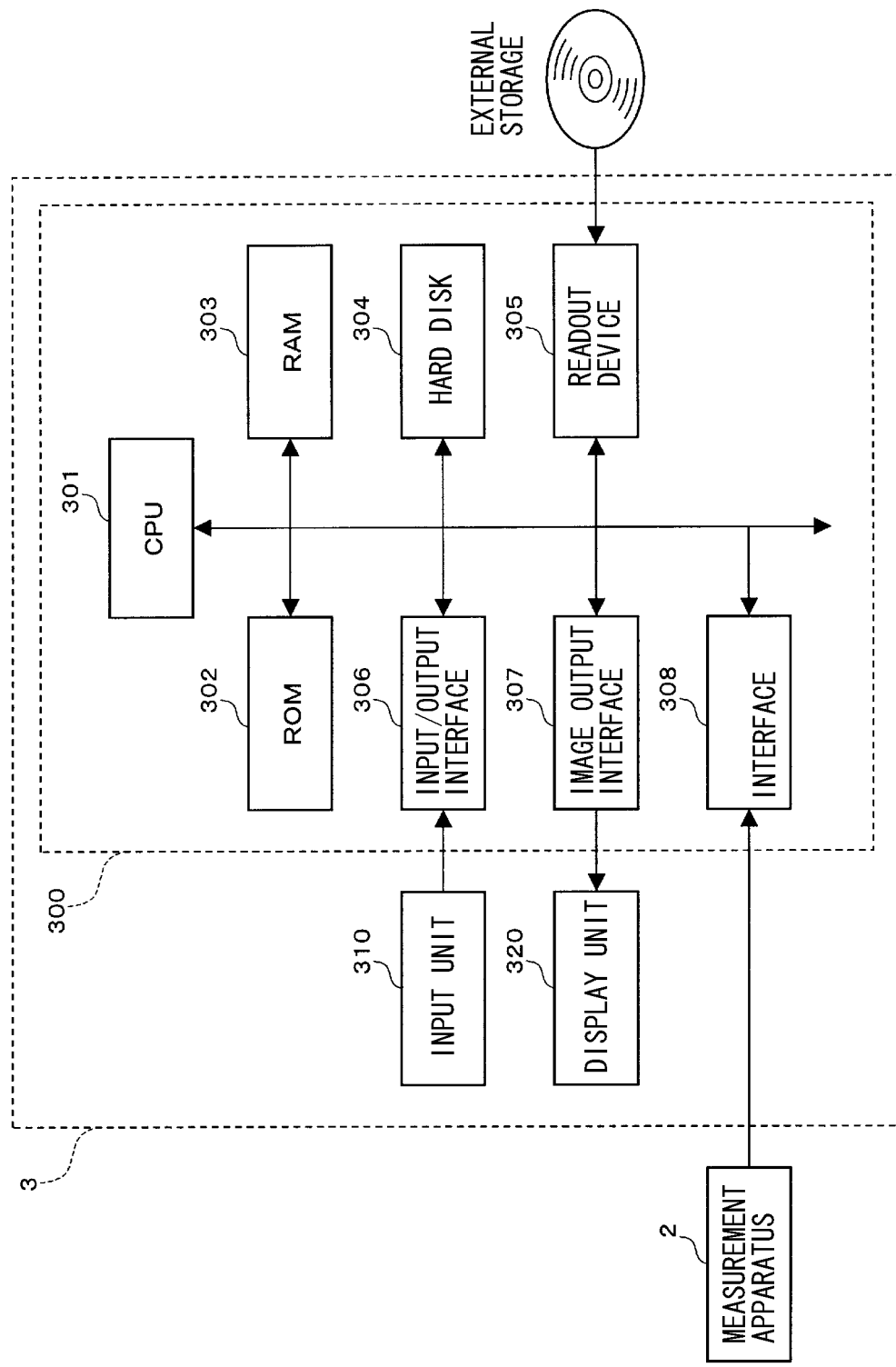
FIG. 4 shows a configuration of an information processing apparatus according to the embodiment.

FIG. 4 shows a configuration of the information processing apparatus 3.

The information processing apparatus 3 is structured as a personal computer, and includes a body 300, an input unit 310, and the display unit 320 (see FIG. 1). The body 300 includes a CPU 301, a ROM 302, a RAM 303, a hard disk 304, a readout device 305, an input/output interface 306, an image output interface 307, and a communication interface 308.

The CPU 301 executes a computer program stored in the ROM 302 and a computer program loaded into the RAM 303. The RAM 303 is used for loading computer programs that are stored in the ROM 302 and the hard disk 304. The RAM 303 is also used as a work area for the CPU 301 when these computer programs are executed.

In the hard disk 304, various computer programs executed by the CPU 301, such as an operating system and application programs, and data used for executing these computer programs, are installed. Further, the hard disk 304 stores measurement data received from the measurement apparatus 2 and a medication administration history which will be described below.

Figure 11:
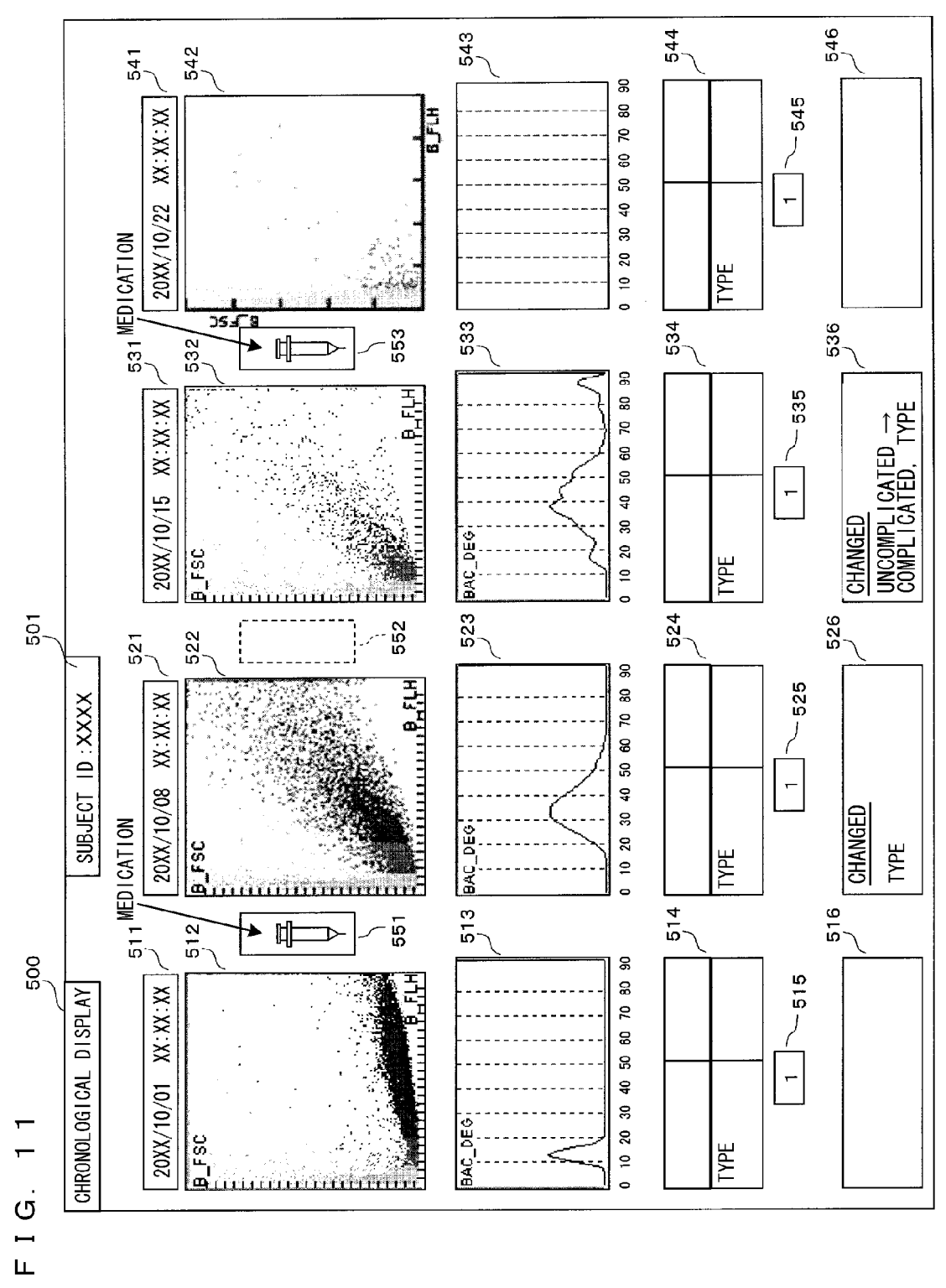

In addition, in the hard disk 304, a program for obtaining based on the measurement data the number of bacteria contained in a sample and for performing analysis of the sample, and a display program for displaying the analysis results on the display unit 320, are installed. These installed programs allow an analysis process and a display process to be performed. These processes will be described below. That is, owing to these programs, the CPU 301 has functions of performing processing as shown in (b) of FIG. 5, FIG. 6, and FIG. 9 as well as functions of displaying screens as shown in FIG. 10 to FIG. 12. These functions will be described below.

The readout device 305 is structured as a CD drive, DVD drive, or the like. The readout device 305 is configured to read a computer program and data that are stored in an external storage, for example, an external storage medium. Accordingly, programs executed by the information processing apparatus 3 can be updated via an external storage, for example, an external storage medium.

The input unit 310, which includes a mouse and a keyboard, is connected to the input/output interface 306. The user uses the input unit 310 to give instructions to the information processing apparatus 3. The image output interface 307 is connected to the display unit 320, which includes a display and the like. The image output interface 307 outputs image signals based on image data to the display unit 320. The display unit 320 displays images based on the image signals that are inputted from the image output interface 307.

By means of the communication interface 308, the information processing apparatus 3 can receive measurement data that is transmitted from the measurement apparatus 2. The received measurement data is stored in the hard disk 304.

FIG. 5 shows flowcharts showing control performed by the CPU 204 of the measurement apparatus 2 and control performed by the CPU 301 of the information processing apparatus 3. A flowchart (a) in FIG. 5 shows a measurement process performed by the CPU 204 of the measurement apparatus 2, and a flowchart (b) in FIG. 5 shows an analysis process performed by the CPU 301 of the information processing apparatus 3.

Referring to (b) in FIG. 5, when a measurement start instruction is provided from the user via the input unit 310 (S11: YES), the CPU 301 transmits a measurement start signal to the measurement apparatus 2 (S12). Next, the CPU 301 determines whether measurement data has been received (S13). If measurement data has not been received (S13: NO), the CPU 301 does not advance the processing.

Referring to (a) in FIG. 5, when the CPU 204 receives the measurement start signal from the information processing apparatus 3 (S21: YES), the CPU 204 performs a sample measurement as described above (S22). When the sample measurement is completed, the CPU 204 transmits measurement data to the information processing apparatus 3 (S23), and returns the processing to S21.

Referring to (b) in FIG. 5, when the CPU 301 receives the measurement data from the measurement apparatus 2 (S13: YES), the CPU 301 stores the measurement data in the hard disk 304, and performs the analysis process based on the measurement data (S14). Then, the CPU 301 causes the display unit 320 to display analysis results obtained at S14 (S15), and causes the display unit 320 to display change information based on the analysis results (S16). Thereafter, the processing returns to S11. Note that the analysis process performed at S14 is described below with reference to FIG. 6, and the process of displaying change information that is performed at S16 is described below with reference to FIG. 9.

Figure 6:
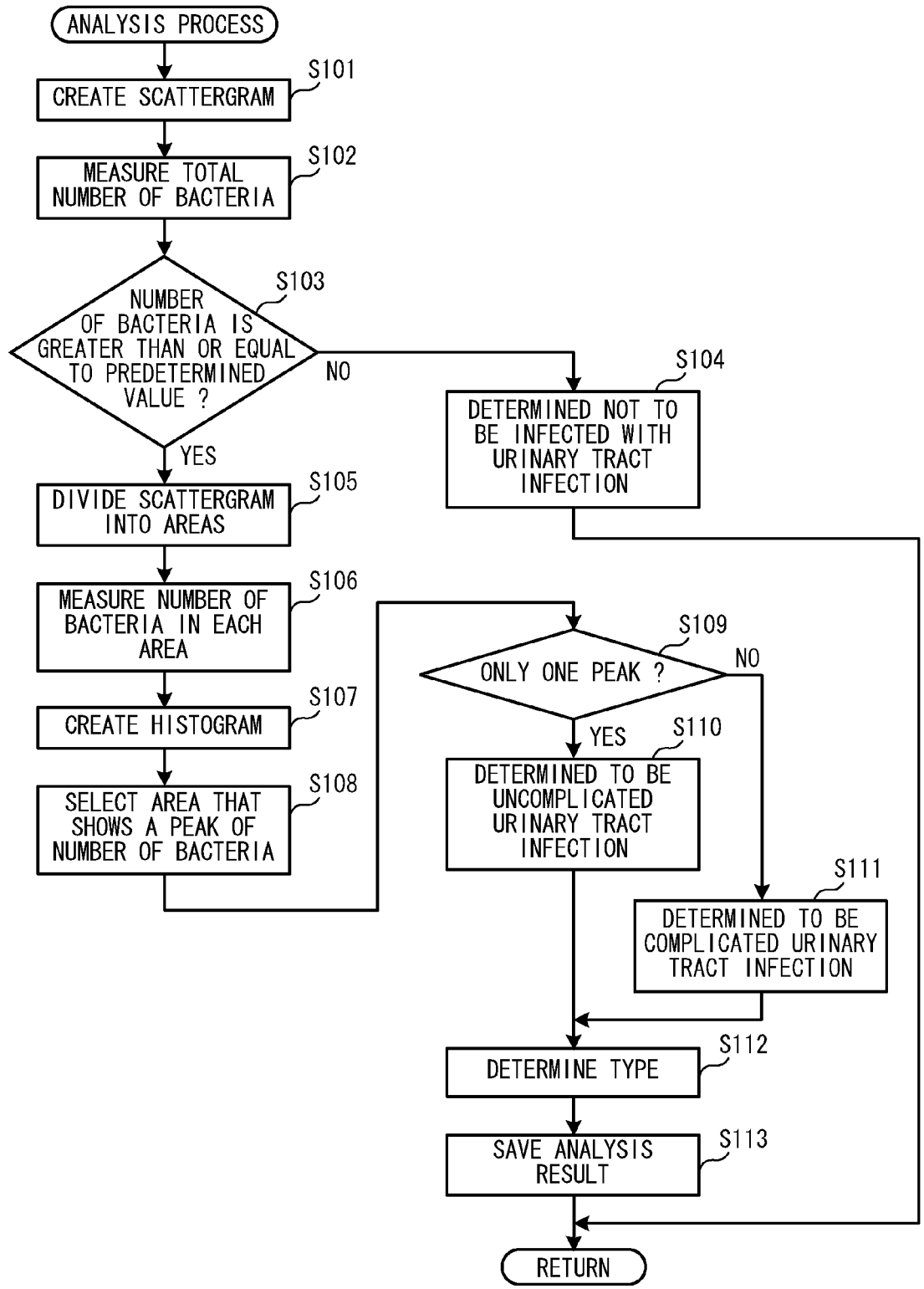
FIG. 6 is a flowchart showing the analysis process according to the embodiment.

FIG. 6 is a processing flowchart showing the analysis process performed at S14 of FIG. 5.

Figure 7A:
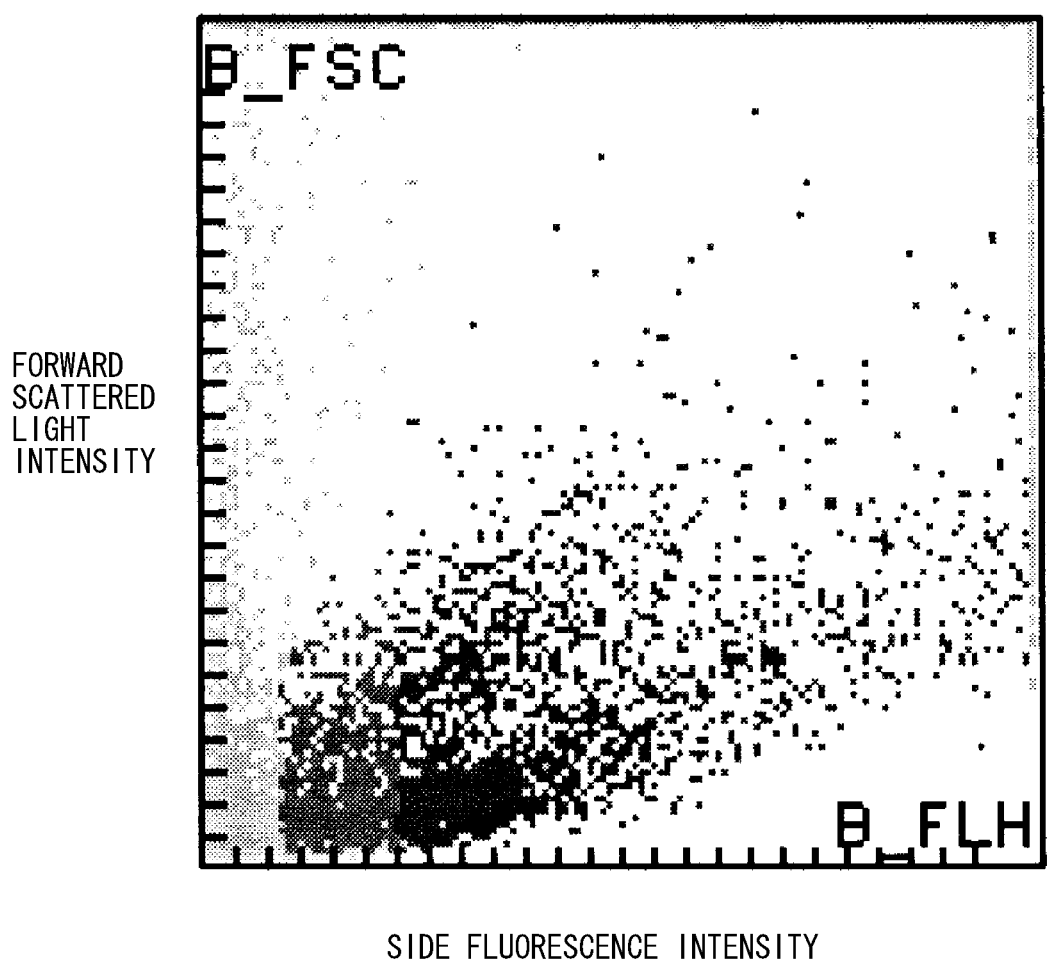
FIG. 7A shows a scattergram according to the embodiment.

First, the CPU 301 loads the measurement data from the hard disk 304 into the RAM 303. Based on the loaded measurement data, the CPU 301 creates a two-dimensional scattergram of which the vertical axis represents forward scattered light intensity and the horizontal axis represents side fluorescence intensity (S101). In the two-dimensional scattergram, pieces of the measurement data are plotted. Each piece of the measurement data indicates a forward scattered light intensity and a side fluorescence intensity of a single bacterium. FIG. 7A shows an example of the scattergram created at S101. Based on the created two-dimensional scattergram, the CPU 301 measures the total number of bacteria contained in the measurement sample (S102).

Next, the CPU 301 determines whether the number of bacteria contained in the measurement sample is greater than or equal to a predetermined value (S103). To be specific, the CPU 301 obtains the number of bacteria contained in 1 mL of the sample from the total number of bacteria measured at S102, and determines whether the number of bacteria contained in 1 mL of the sample is greater than or equal to the predetermined value. Note that, in the present embodiment, the predetermined value used in the determination at S103 is a threshold bacterial count that is used for determining whether a subject from whom the sample was collected is infected with a urinary tract infection. The threshold bacterial count is, for example, $1.0 \times 10^4$ in 1 mL of the sample.

If the CPU 301 determines that the number of bacteria contained in the measurement sample is not greater than or equal to the predetermined value (S103: NO), then the CPU 301 determines that the subject is not infected with a urinary tract infection (S104) and ends the processing. On the other hand, if the CPU 301 determines that the number of bacteria contained in the measurement sample is greater than or equal to the predetermined value (S103: YES), the processing proceeds to S105.

Next, the CPU 301 divides the two-dimensional scattergram created at S101 into a plurality of areas by using predetermined slope angles (S105). The CPU 301 measures the number of bacteria contained in each of the areas of the two-dimensional scattergram divided at S105 (S106).

Hereinafter, the plurality of areas of the scattergram will be described with reference to FIG. 7B and FIG. 7C.

Figure 7B:
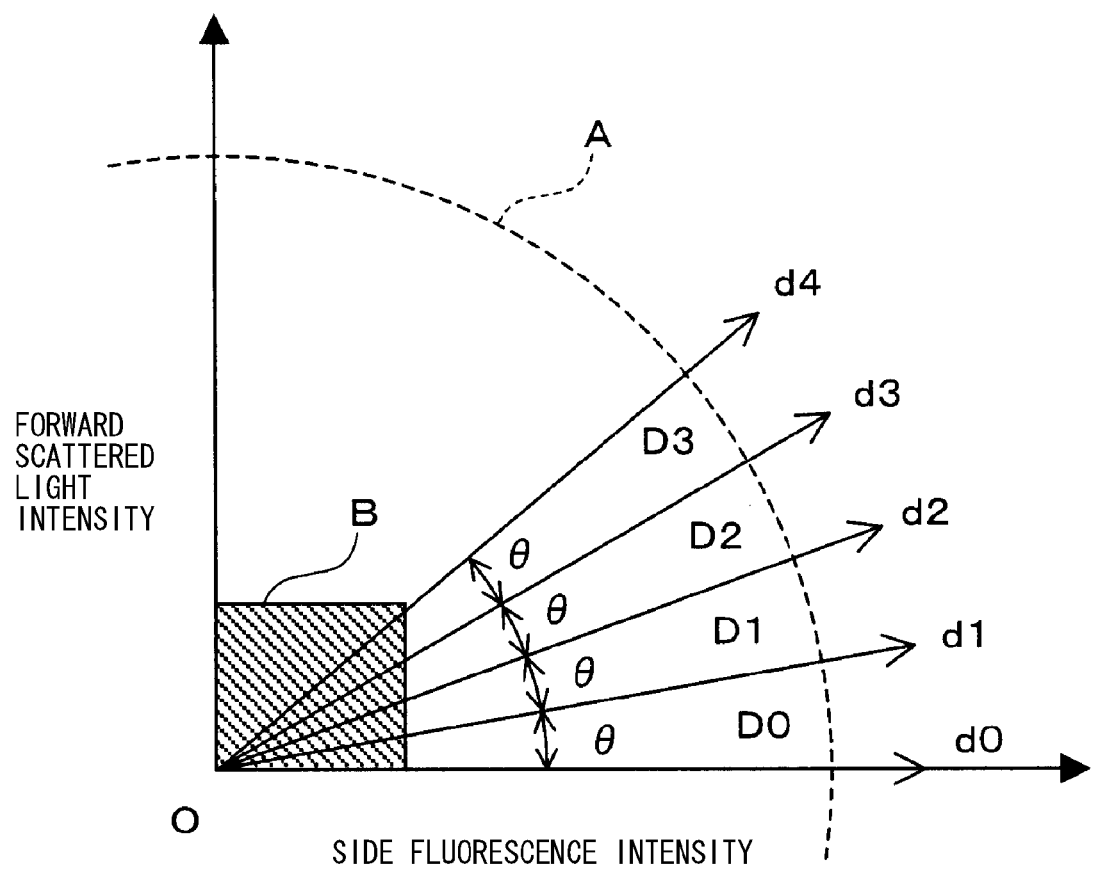
FIG. 7B illustrates dividing the scattergram according to the embodiment.

FIG. 7B is a schematic diagram showing the scattergram divided at S105.

In FIG. 7B, straight lines d0, d1, d2, d3, d4, etc., are straight lines each extending in a radial direction of a virtual circle A whose center is the origin (i.e., origin O) of the scattergram. The straight line d0 coincides with the horizontal axis of the scattergram. As shown in FIG. 7B, each of the other straight lines forms an angle θ with straight lines adjacent thereto. Areas D0, D1, D2, D3, etc., are a result of dividing the scattergram by the straight lines d0, d1, d2, d3, d4, etc. Note that the angle θ may be set to any angle, for example, 1 degree or 10 degrees. After the scattergram is divided into the plurality of areas in this manner, a rectangular area B which contains the origin O is excluded from the areas D0, D1, D2, D3, etc.

Figure 7C:
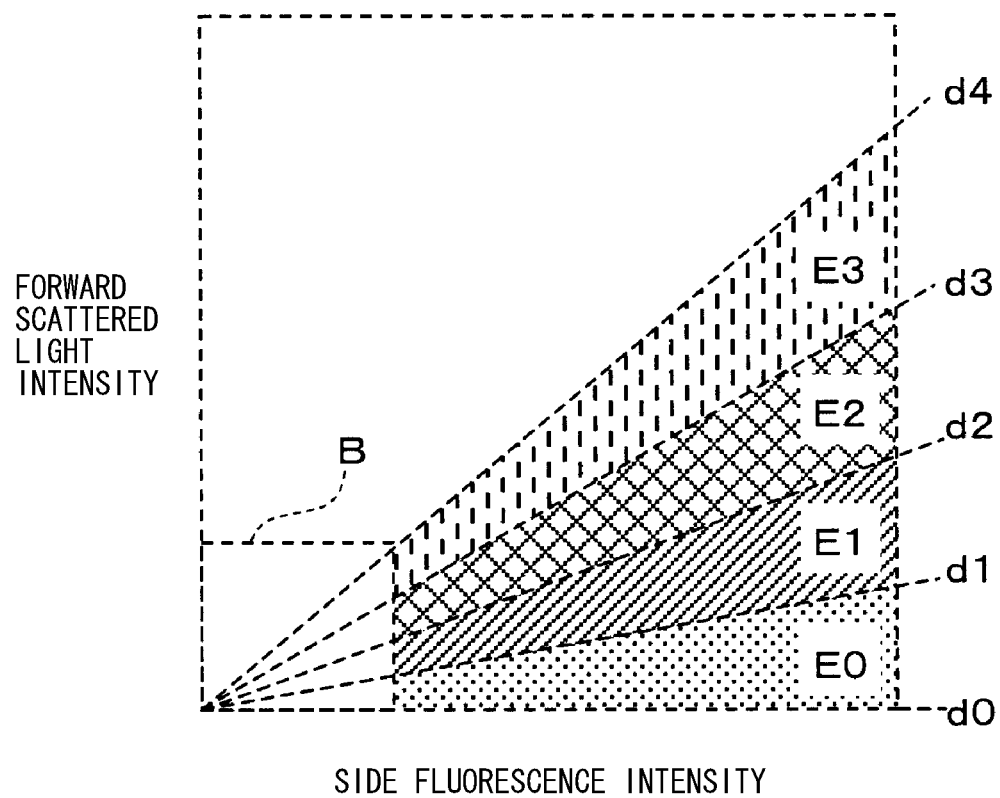
FIG. 7C shows areas each used for measuring the number of bacteria on the scattergram, according to the embodiment.

FIG. 7C shows areas each used for measuring the number of bacteria on the scattergram. As shown in FIG. 7C, areas E0, E1, E2, E3, etc., which are each used for measuring the number of bacteria, are a result of excluding the area B from the areas D0, D1, D2, D3, etc., shown in FIG. 7B.

Here, the area B is excluded from the areas D0, D1, D2, D3, etc., of FIG. 7B for the purpose of improving the accuracy of determination of the classification of a urinary tract infection and the accuracy of determination of types of bacteria. These determinations will be described below. To be specific, as shown in the scattergram of FIG. 7A, distributions of bacteria tend to concentrate near the origin O. For this reason, if bacteria distributed near the origin O are counted in each of the areas D0, D1, D2, D3, etc., then differences are not likely to occur among the counting results of the respective areas. This hinders smooth determination of bacteria. Moreover, in the area B, as compared to other areas (i.e., areas where the forward scattered light intensity and the side fluorescence intensity are greater than those in the area B), areas divided by the straight lines d0, d1, d2, d3, d4, etc., are small. Furthermore, distributions of different types of bacteria tend to overlap each other near the origin O. Therefore, if bacteria are counted in an area near the origin, it is likely that a large number of bacteria that are not intended to be counted in the area are counted. This causes a significant error in the counting result.

For the above reasons, the area B is excluded from the areas D0, D1, D2, D3, etc., so that bacteria near the origin O are not counted in the determination of the classification of a urinary tract infection and the determination of types of bacteria, which determinations are described below, and so that the numbers of bacteria contained in the respective areas, which are obtained from the counting, may significantly differ from each other.

Note that the size of the area B is set such that types of bacteria that are determined based on the numbers of bacteria contained in the respective areas E0, E1, E2, E3, etc., are closest to those determined based on measurement results that would be obtained by a measurement method in which cultured bacteria are used.

Returning to FIG. 6, next, the CPU 301 creates a histogram based on the numbers of bacteria that are obtained at S106 for the areas E0, E1, E2, E3, etc., respectively (S107).

Figure 8A:
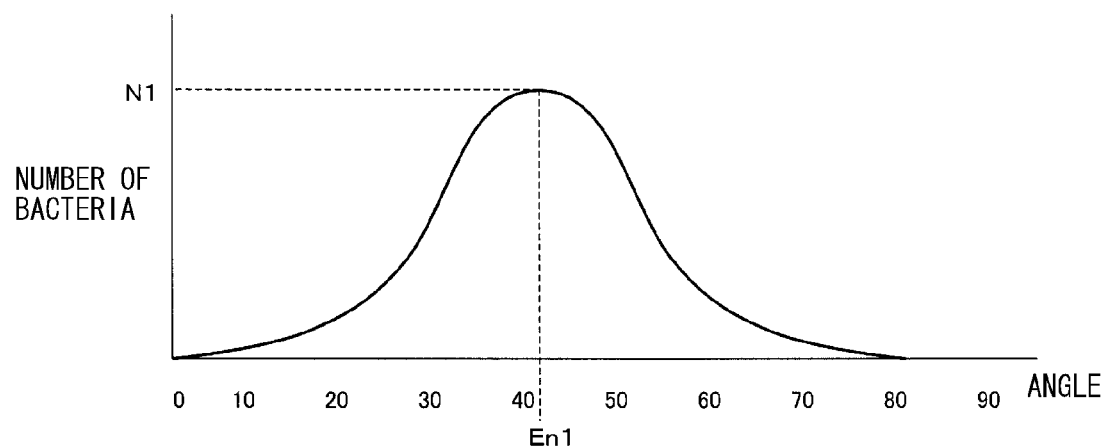
FIG. 8A shows an example of a histogram according to the embodiment.

FIG. 8A shows an example of the histogram created at S107. In FIG. 8A, the horizontal axis represents angles, with respect to the straight line d0, of the straight lines d0, d1, d2, d3, d4, etc., which divide the areas E0, E1, E2, E3, etc. That is, the horizontal axis corresponds to the areas E0, E1, E2, E3, etc., in order of their angle with respect to the straight line d0, from the smallest angle to the greatest angle. The vertical axis represents the numbers of bacteria that are contained in the areas E0, E1, E2, E3, etc., respectively.

Returning to FIG. 6, next, the CPU 301 selects, in the histogram created at S107, the area(s) that shows a peak of the number of bacteria (S108).

Here, an area that shows a peak of the number of bacteria is an area (an angular range) which corresponds to the peak of a raised portion of the histogram. That is, among the areas E0, E1, E2, E3, etc., an area for which the number of bacteria counted therein is greater than the number of bacteria counted in adjacent areas that precede and follow the area in terms of the size of the angle with respect to the straight line d0, is selected as a peak area.

Figure 8B:
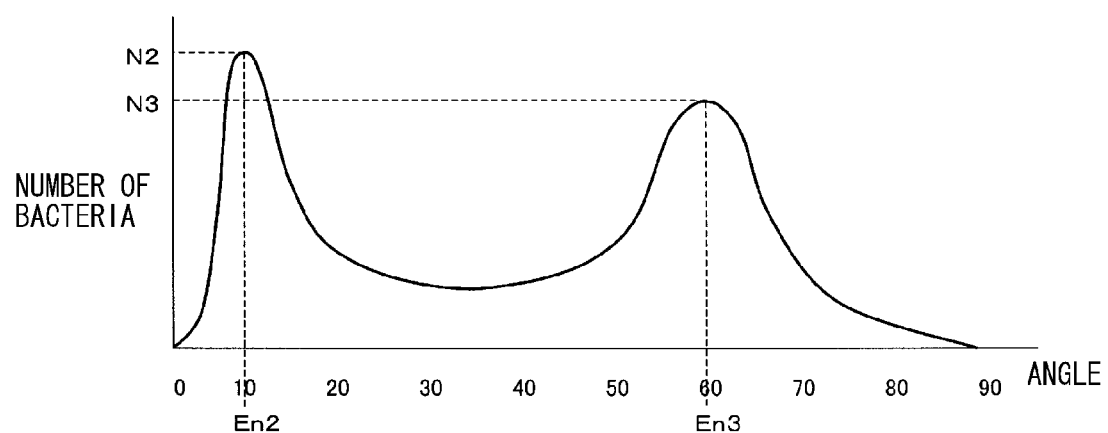
FIG. 8B shows an example of a histogram according to the embodiment.

For example, the histogram of FIG. 8A shows a single peak of the number of bacteria. At the peak, the bacterial count is N1. In this case, the CPU 301 selects an area En1 that corresponds to the peak. FIG. 8B shows another example of a histogram. The histogram of FIG. 8B shows two peaks of the number of bacteria. At these two peaks, the bacterial counts are N2 and N3, respectively. In this case, the CPU 301 selects an area En2 which corresponds to the peak at the left of the histogram and an area En3 which corresponds to the peak at the right of the histogram.

Next, if the number of areas selected at S108 as corresponding to a peak of the number of bacteria is one (S109: YES), then the CPU 301 determines that the classification of a urinary tract infection indicated by the sample from which the measurement data has been obtained is an uncomplicated urinary tract infection (S110). On the other hand, if the number of areas selected at S108 as corresponding to a peak of the number of bacteria is two or more (S109: NO), then the CPU 301 determines that the classification of a urinary tract infection indicated by the sample from which the measurement data has been obtained is a complicated urinary tract infection (S111).

Subsequently, based on the area(s) selected at S108, the CPU 301 determines the type(s) of bacteria contained in the sample from which the measurement data has been obtained (S112). To be specific, the CPU 301 determines the type(s) of bacteria contained in the sample based on whether the angular range, with respect to the straight line d0, of the area(s) selected at S108 is included among angular ranges that are preset for the purpose of specifying bacterial types. For example, in the case of FIG. 7B, the angular range of the area D2 is 2θ to 3θ. If the area D2 is selected at S108, the type of bacteria contained in the area D2 is determined based on which angular range, among the angular ranges that are preset for the purpose of specifying bacterial types, includes the angular range of 2θ to 3θ.

In the present embodiment, the angular ranges used for specifying bacterial types are set as shown below.

(a) 0° to 25° . . . Bacilli
(b) 26° to 44° . . . Streptococci
(c) 45° to 80° . . . Staphylococci
(d) 81° to 90° . . . Not Applicable Note that, in the present embodiment, if the number of areas selected at S108 is three or more, then bacterial types are determined only for the areas for which the numbers of bacteria counted therein are the greatest and the second greatest among the selected areas. However, as an alternative, bacterial types may be determined for the areas for which the numbers of bacteria counted therein are the greatest, the second greatest, and the third greatest among the selected areas. As a further alternative, bacterial types may be determined for all of the select areas.

Next, the CPU 301 stores the analysis results in the hard disk 304 (S113), which analysis results contain the classification of urinary tract infection and the bacterial type(s) obtained in the above manner. Then, the processing ends.

Figure 9:
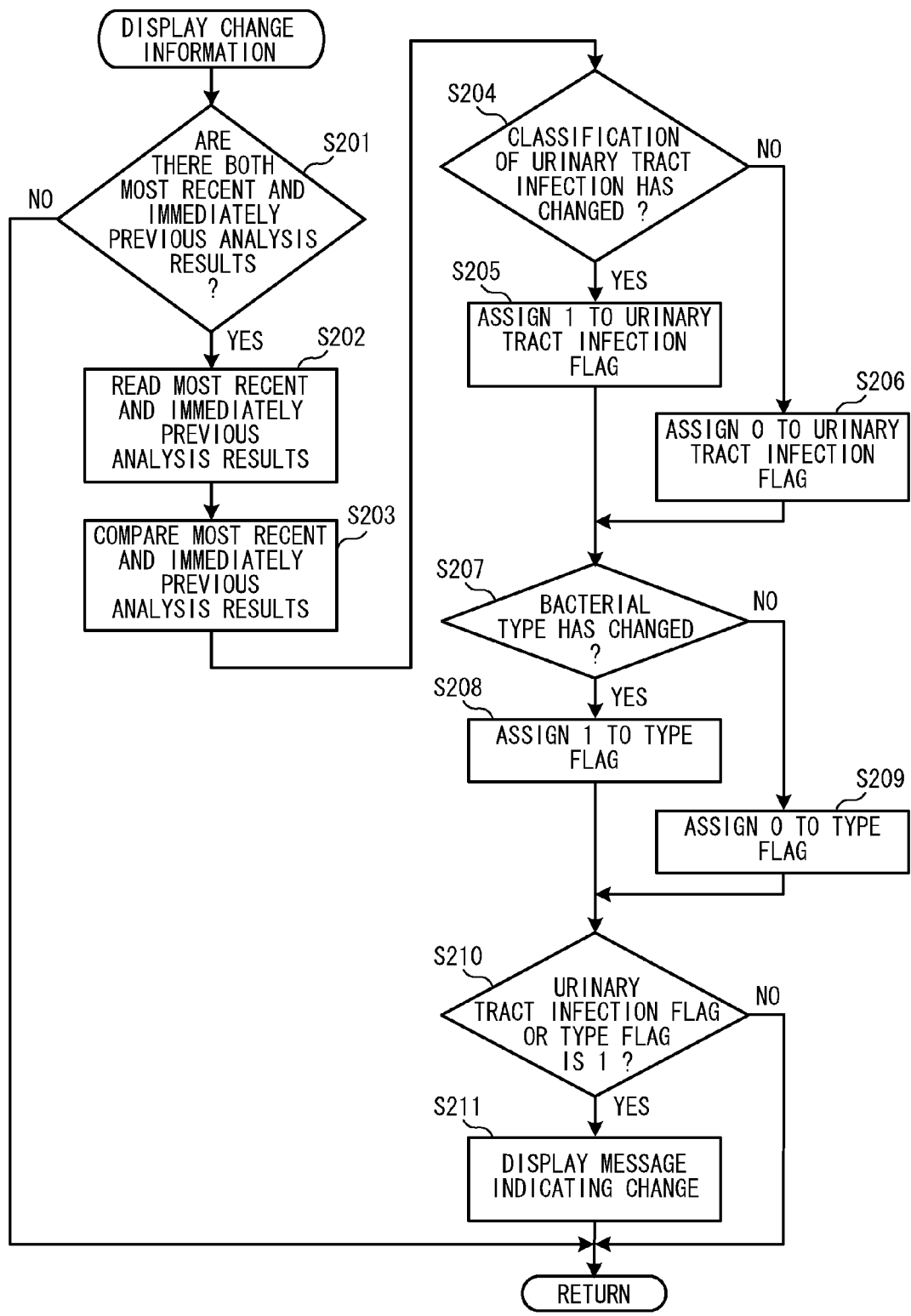
FIG. 9 is a flowchart showing a process of displaying change information according to the embodiment.
Figure 10:
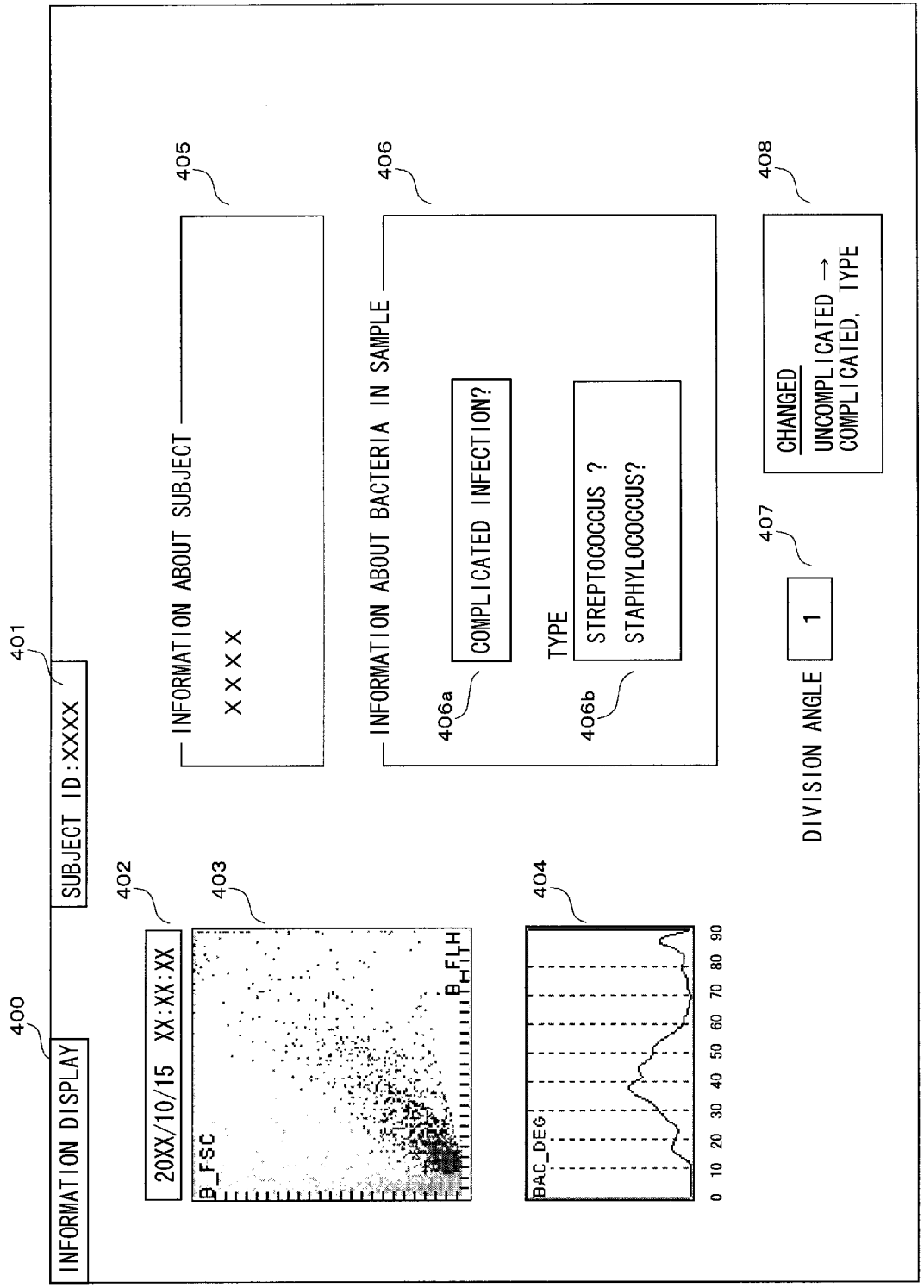
FIG. 10 shows an example of an information display screen displayed by a display unit of the information processing apparatus according to the embodiment.

FIG. 9 is a processing flowchart showing the process of displaying change information that is performed at S16 of FIG. 5.

First, the CPU 301 determines whether the analysis results obtained from the most recently performed analysis and the analysis results obtained from the immediately previously performed analysis are all stored in the hard disk 304 regarding the subject from whom the sample was collected for the most recently performed analysis (S201). If the analysis results obtained from the most recently performed analysis and the analysis results obtained from the immediately previously performed analysis are not all stored in the hard disk 304 (S201: NO), the processing ends. If the analysis results obtained from the most recently performed analysis and the analysis results obtained from the immediately previously performed analysis are all stored in the hard disk 304 (S201: YES), the CPU 301 loads the most recent analysis results and the immediately previous analysis results into the RAM 303 (S202), and compares the most recent analysis results and the immediately previous analysis results (S203).

Next, based on the result of the comparison at S203, the CPU 301 determines whether the classification of urinary tract infection indicated by the most recent analysis results has changed from that indicated by the immediately previous analysis results (S204). If it is determined that the classification of urinary tract infection has changed (S204: YES), the CPU 301 assigns 1 to a urinary tract infection flag (S205). On the other hand, if it is determined that the type of urinary tract infection has not changed (S204: NO), the CPU 301 assigns 0 to the urinary tract infection flag (S206).

Subsequently, the CPU 301 determines based on the result of the comparison at S203 whether the bacterial type indicated by the most recent analysis results has changed from that indicated by the immediately previous analysis results (S207). If it is determined that the bacterial type has changed (S207: YES), the CPU 301 assigns 1 to a type flag (S208). On the other hand, if it is determined that the bacterial type has not changed (S207: NO), the CPU 301 assigns 0 to the type flag (S209).

Next, the CPU 301 determines whether the urinary tract infection flag is 1 or the type flag is 1 (S210). If it is determined that either the urinary tract infection flag is 1 or the type flag is 1 (S210: YES), the CPU 301 causes the display unit 320 of the information processing apparatus 3 to display a message indicating the change (S211). Then, the processing ends.

FIG. 10 shows an example of an information display screen 400 displayed by the display unit 320 of the information processing apparatus 3. The information display screen 400 is displayed in accordance with S15 and S16 of FIG. 5.

The information display screen 400 includes a subject ID area 401, a measurement date/time area 402, a scattergram area 403, a histogram area 404, a subject information area 405, a bacterial information area 406, a division angle area 407, and a change information area 408. The bacterial information area 406 includes a urinary tract infection classification area 406a and a type area 406b.

The subject ID area 401 shows a subject ID. The subject ID identifies the subject from whom the sample was collected for the analysis of which the results are shown in the information display screen 400. The measurement date/time area 402 shows the date and time when the measurement for the analysis was performed. The scattergram area 403 shows a scattergram as in FIG. 7A which is obtained based on the performed measurement. The histogram area 404 shows a histogram as in FIG. 8A or 8B which is obtained based on the scattergram shown in the scattergram area 403.

The subject information area 405 shows, for example, the name of the subject, the name of the attending doctor, and comments from the attending doctor that are associated with the subject ID. In addition to these types of information, information about medication administered to the subject may be inputted via the input unit 310 (see FIG. 4) and shown in the subject information area 405.

The urinary tract infection classification area 406a shows the determination result obtained at S110 or 5111 of the analysis process shown in FIG. 6. That is, in a case where the classification of the urinary tract infection indicated by the sample analyzed in the analysis process is an uncomplicated urinary tract infection, the urinary tract infection classification area 406a shows "UNCOMPLICATED INFECTION?". On the other hand, in a case where the classification of the urinary tract infection indicated by the sample analyzed in the analysis process is a complicated urinary tract infection, the urinary tract infection classification area 406a shows "COMPLICATED INFECTION?".

Note that "?" added at the end of the message shown in the urinary tract infection classification area 406a indicates to the user that the sample indicates a high possibility that the subject is infected with an uncomplicated urinary tract infection or a complicated urinary tract infection. If there is no determination provided regarding the classification of urinary tract infection, or the urinary tract infection of the sample cannot be determined to be a specific classification, then the urinary tract infection classification area 406a is left blank or shows a message "UNKNOWN".

The type area 406b shows the bacterial type(s) determined at S112 of the analysis process shown in FIG. 6. Note that "?" added at the end of the message shown in the type area 406b indicates that there is a high possibility that the sample contains the bacteria of the type(s) shown in the type area 406b.

If there is no determination provided regarding the bacterial types, or the bacteria contained in the sample cannot be determined to be a specific type(s), the type area 406b is left blank or shows a message "UNKNOWN".

The division angle area 407 shows the angle θ which is formed between each of the straight lines d0, d1, d2, d3, d4, etc., and the respective straight line(s) adjacent thereto. The straight lines d0, d1, d2, d3, d4, etc., divide the areas D0, D1, D2, D3, etc., as shown in FIG. 7B.

The change information area 408 shows, in accordance with the process of displaying change information which is performed as shown in FIG. 9, a message indicating that the bacterial type has changed. Here, as shown in FIG. 10, the change information area 408 shows "CHANGED" indicating that the most recent analysis results have changed from the immediately previous analysis results. In a case where the classification of urinary tract infection has changed from an uncomplicated infection to a complicated infection, the change information area 408 shows "UNCOMPLICATED→COMPLICATED" together with "CHANGED". In a case where the bacterial type has changed, the change information area 408 shows "TYPE" together with "CHANGED". Note that if the analysis results obtained based on the most recent measurement have not changed from the analysis results obtained based on the immediately previous measurement, or if the number of bacteria determined based on the most recent measurement is not greater than or equal to the predetermined value (NO at S103), then the change information area 408 is left blank.

FIG. 11 shows an example of a chronological display screen 500 which is displayed by the display unit 320 of the information processing apparatus 3. This screen is displayed when an input operation for displaying a chronological display regarding a particular subject is performed via the input unit 310 of the information processing apparatus 3.

The chronological display screen 500 includes: a subject ID area 501; measurement date/time areas 511, 521, 531, and 541; scattergram areas 512, 522, 532, and 542; histogram areas 513, 523, 533, and 543; bacterial information areas 514, 524, 534, and 544; division angle areas 515, 525, 535, and 545; change information areas 516, 526, 536, and 546; and medication information areas 551, 552, and 553.

Similar to the subject ID area 401 shown in FIG. 10, the subject ID area 501 shows a subject ID. The subject ID identifies the subject from whom samples were collected for analyses of which the results are shown in the chronological display screen 500.

Each of the four groups of areas 511 to S16, 521 to S26, 531 to S36, and 541 to S46 shows measurement results and analysis results obtained based on a corresponding single measurement. That is, these four groups show four sets of information that are based on four sets of measurement data obtained from four samples that were collected from the same subject at four different dates and times. Each group shows a corresponding one of the four sets of information, in the areas that correspond to the areas 402, 403, 404, 406, 407, and 408 of the information display screen 400 shown in FIG. 10. Note that, in the present embodiment, the four sets of measurement data that correspond to these four groups are chronologically successive.

Each of the change information areas 516, 526, 536, and 546 shows whether the bacterial type information obtained based on the most recent measurement has changed from the bacterial type information obtained based on the immediately previous measurement, and if the bacterial type information has changed, shows the details of the change. If the bacterial type information obtained based on the most recent measurement has not changed from the bacterial type information obtained based on the immediately previous measurement, or the number of bacteria determined based on the most recent measurement is not greater than or equal to the predetermined value (NO at S103), then the change information area is left blank.

In the example of FIG. 11, in comparison with the analysis results shown at the leftmost position in FIG. 11, the analysis results shown at the second-from-left position in FIG. 11 indicate a change in the bacterial type from "*BACILLUS?*" to "*STREPTOCOCCUS?*". Accordingly, the change information area 526 shows "TYPE" indicating that the bacterial type has changed.

Similarly, since the bacterial type information has changed, as shown in the bacterial information area 534, from the bacterial type information indicated in the bacterial information area 524, the change information area 536 at the third-from-left position in FIG. 11 shows "TYPE" indicating that the bacterial type has changed, and also shows that the classification of urinary tract infection has changed. To be specific, in this case, the classification of urinary tract infection has changed from "UNCOMPLICATED?" to "COMPLICATED?", and the bacterial type has changed from "*STREPTOCOCCUS?*" to "*STREPTOCOCCUS? STAPHYLOCOCCUS?*". Therefore, the change information area 536 shows "UNCOMPLICATED→COMPLICATED" indicating that the classification of urinary tract infection has changed from an uncomplicated urinary tract infection to a complicated urinary tract infection, together with "TYPE" indicating that the bacterial type has changed.

Each of the medication information areas 551, 552, and 553 shows information as to whether medication was administered to the subject between a measurement and a measurement immediately previous thereto. In the example of FIG. 11, information indicating that medication was administered to the subject (in this example, a picture of a syringe) between the measurement date/time indicated in the measurement date/time area 511 and the measurement date/time indicated in the measurement date/time area 521, is shown in the medication information area 551. Similarly, information indicating that medication was administered to the subject between the measurement date/time indicated in the measurement date/time area 531 and the measurement date/time indicated in the measurement date/time area 541, is shown in the medication information area 553.

FIG. 12 shows an example of a medication administration history screen 600 which is displayed by the display unit 320 of the information processing apparatus 3.

The medication administration history screen 600 contains a subject ID area 601, a medication administration history area 602, and an edit command area 603.

The subject ID area 601 shows a subject ID that identifies a subject to whom medications were administered. The medication administration history area 602 shows a history of medications administered to the subject identified by the subject ID indicated in the subject ID area 601.

In the medication administration history area 602, dates and times when the medications were administered to the subject are shown in association with the details of the administered medications. Such medication administration history is stored in the hard disk 304 of the information processing apparatus 3.

Note that, while the screen shown in FIG. 11 is displayed, if the user uses the input unit 310 of the information processing apparatus 3, thereby pressing (e.g., by a click), among the medication information areas 551, 552, and 553, one of the medication information areas 551 and 553 that are showing information (i.e., a picture of a syringe), then the screen shown in FIG. 12 is displayed. Here, in response to one of the medication information areas 551 and 553 being pressed in the screen shown in FIG. 11, a row showing a medication administration date/time and the details of administered medication that correspond to the pressed medication information area, is selectively displayed as shown in FIG. 12. In this manner, the user can check the details of the medication.

The edit command area 603 includes "ADD", "EDIT", and "DELETE" buttons for editing the information shown in the medication administration history area 602. The user can edit the information shown in the medication administration history area 602 by pressing (e.g., by a click) these buttons via the input unit 310. Note that if the information in the medication administration history area 602 is altered, the information shown in the medication information areas 551, 552, and 553 of the chronological display screen 500 of FIG. 11 is also altered so as to be consistent with the alteration of the information in the medication administration history area 602.

As described above, in the present embodiment, the analysis process as shown in FIG. 6 is performed based on the forward scattered light and the side fluorescence that are received by the PD 203f and the PMT 203k, respectively. According to the analysis results obtained from the analysis process, the information display screen 400 as shown in FIG. 10 is displayed by the display unit 320 of the information processing apparatus 3. If a change in the bacterial type has occurred, the change information area 408 shows a message indicating the change. Accordingly, if treatment was given to the subject from whom the sample was collected, the user can check whether the treatment has been effective for the subject.

Further, according to the present embodiment, the chronological display screen 500 as in FIG. 11 shows measurement results and analysis results based on measurement data obtained from four samples that were collected from the same subject at four different dates and times. Accordingly, if treatment was given to the subject from whom the samples were collected, the user can check, chronologically, whether the treatment has been effective for the subject.

Still further, according to the present embodiment, the medication information areas 551, 552, and 553 in the chronological display screen 500 as in FIG. 11 show medication information. Since the medication information is shown in this manner, the user can readily know how the types of bacteria found in the samples have changed owing to medications administered to the subject. This also allows the user to check if the medication administered to the subject has been effective.

Although the embodiment of the present invention has been described as above, the present invention is not limited to the above embodiment. Moreover, various modifications of the above embodiment may be made.

For example, although urine is measured in the above embodiment, blood may also or alternatively be measured. Thus, for example, the present invention is applicable to sample testing apparatuses for testing blood samples. Further, the present invention is applicable to sample testing apparatuses for testing other types of samples.

In the above embodiment, it is determined at S109 of FIG. 6 whether the number of peaks of bacterial count in the histogram is one. Based on the determination result, the classification of the urinary tract infection indicated by the sample from which the measurement data has been obtained, is determined. Here, whether the number of peaks of bacterial count in the histogram is one may be determined based on the skewness of the histogram. Moreover, in order to determine the classification of urinary tract infection, the skewness of the histogram may be used in addition to performing the determination at S109 of the above embodiment.

Described below is a method for determining based on the skewness of the histogram whether the number of peaks of bacterial count is one.

In the histogram of the above embodiment, if the number of pieces of data is n; the number of bacteria at each angle is $X_i$; the average number of bacteria is $X_a$; and the standard deviation is $S(X)$, then a skewness $\alpha_3$ is calculated by an equation shown below.

$$\alpha_3 = \left\{ \frac{1}{n} \sum_{i=1}^{n} (X_i - X_a)^3 \right\} / \{S(X)\}^3 \qquad \text{[Equation 1]}$$

If the histogram shows a symmetrical distribution such as a normal distribution, the value of the skewness $\alpha_3$ is 0. If the skewness $\alpha_3$ is a negative value, the distribution has a negative skew, and the histogram has an elongated tail at the left. On the other hand, if the skewness $\alpha_3$ is a positive value, the distribution has a positive skew, and the histogram has an elongated tail at the right.

If the histogram shows a symmetrical distribution, it is likely that the histogram shows only one peak. On the other hand, if the histogram shows a significant positive or negative skew, it is likely that the histogram shows multiples peaks, or that, although the histogram shows only one peak, other peaks are buried in the elongated tails.

Accordingly, if the value of the skewness $\alpha_3$ is within predetermined positive and negative value ranges from 0, the number of peaks may be determined to be one. On the other hand, if the value of the skewness $\alpha_3$ is out of these ranges, the number of peaks may be determined to be plural. That is, proper adjustment of the positive and negative threshold ranges for the skewness $\alpha_3$ that are used for determining whether the number of peaks is plural, makes it possible to determine whether the number of peaks of the histogram is one based on whether the skewness $\alpha_3$ is within these threshold ranges.

Figure 13A:
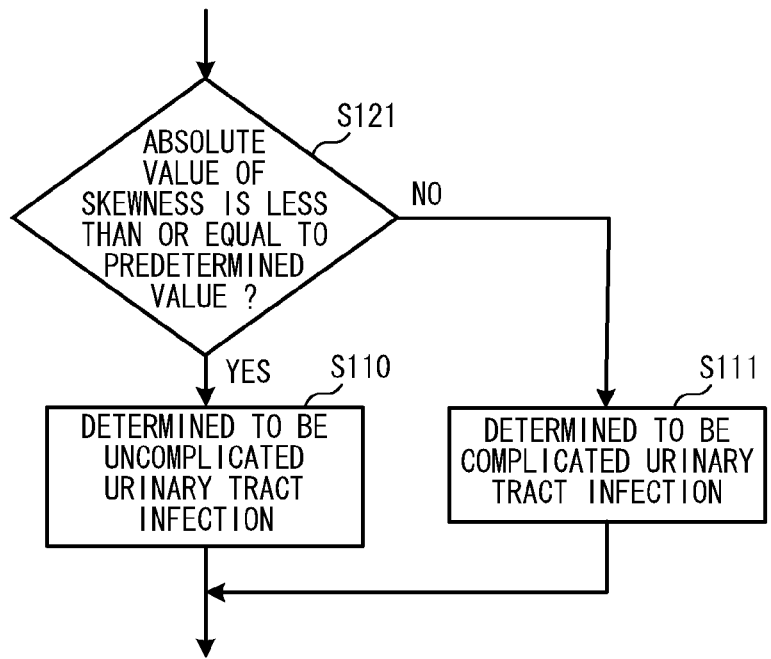
FIG. 13A shows a variation of the flowchart showing the analysis process according to the embodiment.

FIG. 13A is part of a processing flowchart showing the analysis process in which S121, instead of S108 and S109 of FIG. 6, is performed in order to determine whether the number of peaks is one. If the absolute value of the skewness of the histogram created at S107 is less than or equal to a predetermined value (i.e., a threshold) (S121: YES), the number of peaks of the histogram is determined to be one. Then, the classification of the urinary tract infection indicated by the sample from which the measurement data has been obtained is determined to be an uncomplicated urinary tract infection (S110). On the other hand, if the absolute value of the skewness of the histogram created at S107 is not less than or equal to the predetermined value (S121: NO), the number of peaks of the histogram is determined to be plural. Then, the classification of the urinary tract infection indicated by the sample from which the measurement data has been obtained is determined to be a complicated urinary tract infection (S111).

In the above determination process, even in a case where the histogram shows multiple peaks due to noise or the like, the number of peaks is determined to be one if the shape of the histogram is substantially symmetrical. Accordingly, the classification of the urinary tract infection indicated by the sample from which the measurement data has been obtained is determined to be an uncomplicated urinary tract infection. Further, even in a case where the histogram shows only one peak, the number of peaks is determined to be plural if other peaks are buried in the elongated tails of the histogram. Then, the classification of the urinary tract infection indicated by the sample from which the measurement data has been obtained is determined to be a complicated urinary tract infection.

Figure 13B:
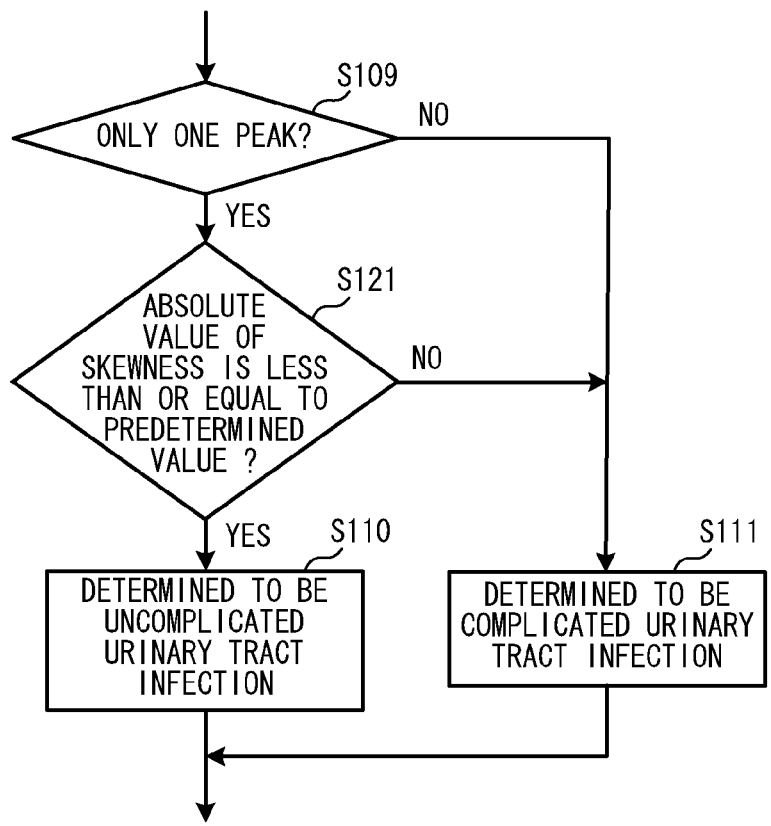
FIG. 13B shows a variation of the flowchart showing the analysis process according to the embodiment.

FIG. 13B is part of a processing flowchart showing the analysis process in which S121 is additionally performed between S109 and 5110 of FIG. 6 in order to determine whether the number of peaks is one. In this case, the shape of the histogram is determined at S121 based on its skewness, in addition to the determination being performed at S109 as to whether the number of peaks of the histogram is one. In this manner, even if the number of peaks is determined to be one, the classification of the urinary tract infection indicated by the sample from which the measurement data has been obtained is determined to be a complicated urinary tract infection if the histogram has elongated tails at the right and left.

In the above embodiment, the chronological display screen 500 of FIG. 11 shows the four sets of measurement results and analysis results for the respective four sets of measurement dates and times, at the same time. However, the number of sets of measurement dates and times for which the measurement results and analysis results are shown is not limited to four. The measurement results and analysis results may be shown at the same time for any multiple number of sets of measurement dates and times. If the measurement results and analysis results to be shown do not entirely fit in a single screen, a scrollbar may be provided on the chronological display screen 500 so as to allow scrolling of the display screen, or a page switching button may be provided so as to allow switching of the page to view.

Further, the chronological display screen 500 shows information based on multiple sets of measurement data that are chronologically successive. However, the chronological display screen 500 may show information based on multiple sets of measurement data that are not chronologically successive. For example, the user may select, among the past measurement dates and times, any four sets of measurement dates and times for which information is to be shown chronologically.

Still further, in the above embodiment, characters are used to show information in the change information area 408 of the information display screen 400 and in the change information areas 516, 526, 536, and 546 of the chronological display screen 500. However, not only characters but also symbols and figures that are easier to visually recognize may be used to show information in these areas.

Still further, in the above embodiment, each of the medication information areas 551, 552, and 553 of the chronological display screen 500 merely indicates that medication has been administered to the subject. However, the present invention is not limited thereto. Each medication information area may show a date and time when medication was administered and the details of the medication. Moreover, when any one of the medication information areas is pressed (e.g., clicked), the date and time when medication was administered and the details of the medication that correspond to the pressed medication information area may be shown as a pop-up.

Still further, in the above embodiment, the change information area 408 of FIG. 10 shows, based on the comparison of the most recent analysis results and the immediately previous analysis results, change information indicating that the most recent analysis results have changed from the immediately previous analysis results. However, the present invention is not limited thereto. The most recent analysis results may be compared with analysis results earlier than the immediately previous analysis results. For example, the most recent analysis results may be compared with analysis results obtained based on measurement performed at any date and time that precede the date and time of the measurement for the most recent analysis results.

Still further, in the above embodiment, each of the change information areas 516, 526, 536, 546, and change information area 408 may show a message "UNCHANGED" if the corresponding analysis results show no changes from the previous analysis results. Alternatively, the display may be performed in such a manner that each of these areas is not shown if the corresponding analysis results show no changes from the previous analysis results.

Still further, in the above embodiment, in the determination as to whether the analysis results have changed, it is determined as shown in S210 of FIG. 9 whether the classification of urinary tract infection or the bacterial type has changed. However, the present invention is not limited thereto. The determination may be additionally performed as to whether the number of bacterial types has changed.

Figure 14:
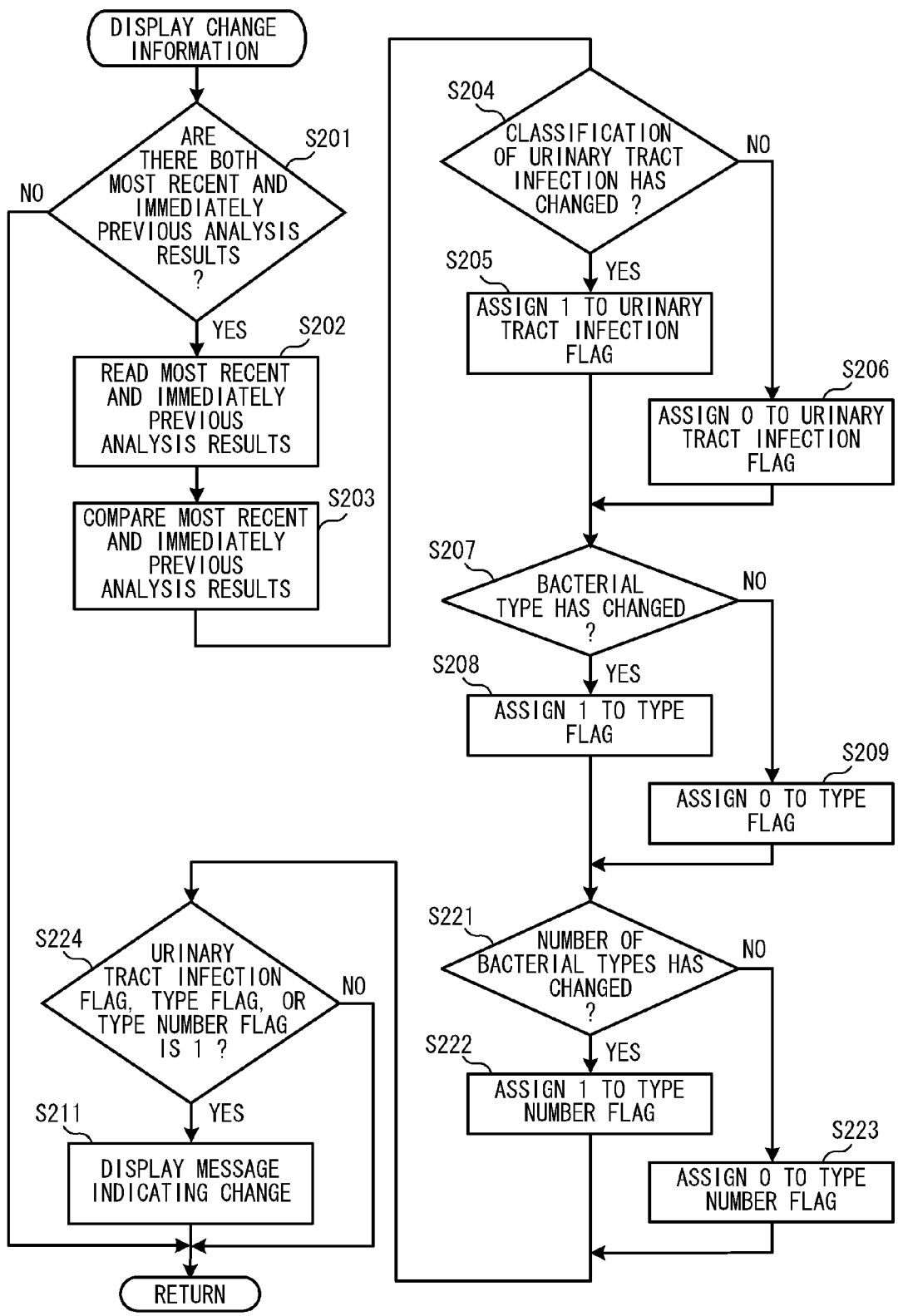
FIG. 14 shows a variation of the flowchart showing the process of displaying change information according to the embodiment.

FIG. 14 is a processing flowchart showing the process of displaying change information in the above case. The flowchart of FIG. 14 is different from the flowchart of FIG. 9 in that S221 to S223 are added and S210 is replaced with S224. Hereinafter, these added and replaced steps are described.

Based on the result of the comparison at S203, the CPU 301 determines whether the number of bacterial types indicated by the most recent analysis results has changed from that indicated by the immediately previous analysis results (S221). If it is determined that the number of bacterial types indicated by the most recent analysis results has changed from that indicated by the immediately previous analysis results (S221: YES), the CPU 301 assigns 1 to a type number flag (S222). On the other hand, if it is determined that the number of bacterial types indicated by the most recent analysis results has not changed from that indicated by the immediately previous analysis results (S221: NO), the CPU 301 assigns 0 to the type number flag.

Next, the CPU 301 determines whether the urinary tract infection flag is 1, or the type flag is 1, or the type number flag is 1 (S224). If it is determined that the urinary tract infection flag is 1, or the type flag is 1, or the type number flag is 1 (S224: YES), the CPU 301 causes the display unit 320 of the information processing apparatus 3 to display a message indicating the change (S221), and ends the processing.

Figure 15:
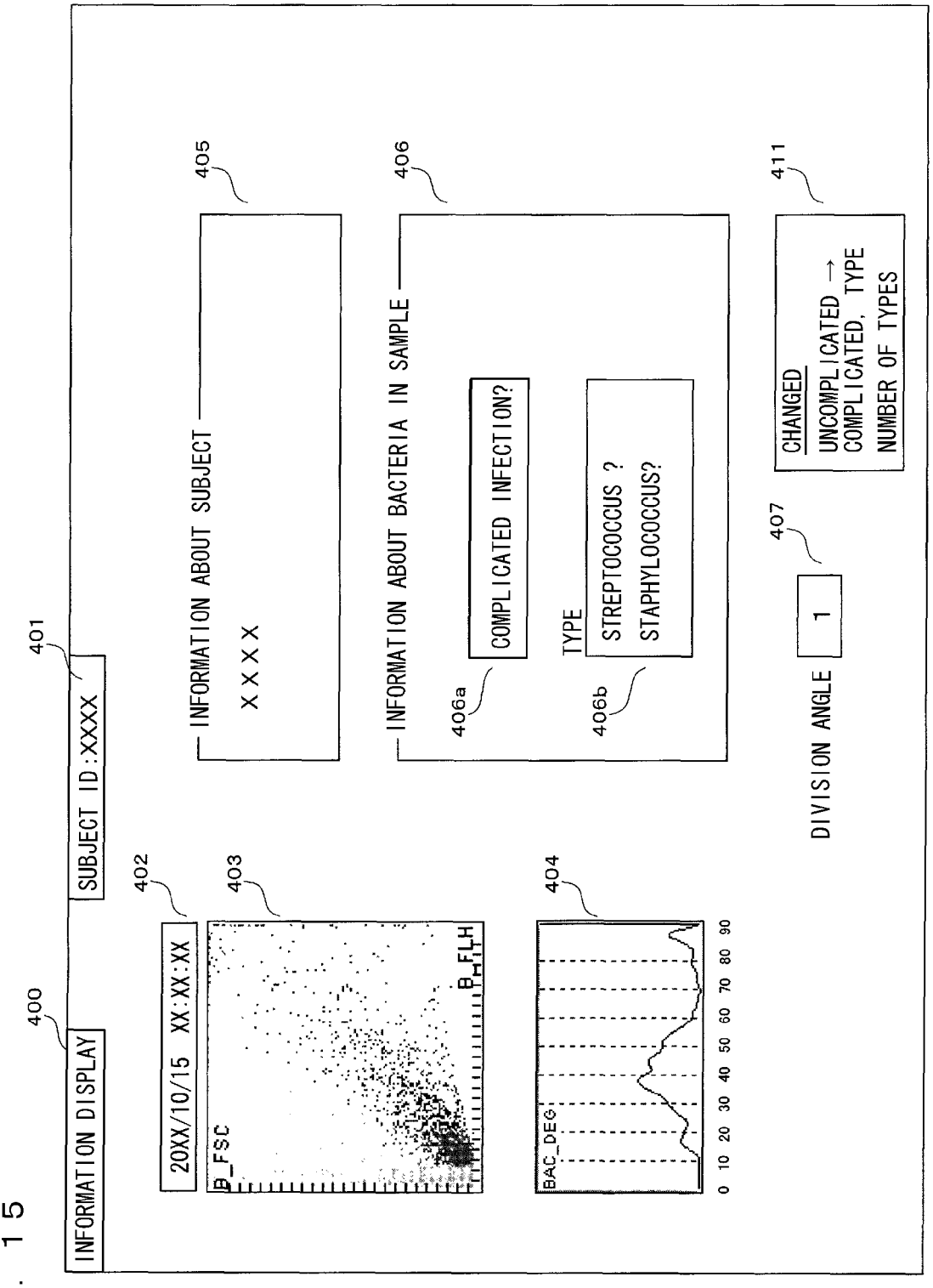
FIG. 15 shows a variation of the information display screen displayed by the display unit of the information processing apparatus according to the embodiment.

FIG. 15 shows an example of the information display screen 400 displayed by the display unit 320 of the information processing apparatus 3 in the above case. FIG. 15 shows, in a change information area 411, information that is different from the information shown in the change information area 408 of FIG. 10.

The change information area 411 shows, in addition to the information shown in the change information area 408 of FIG. 10, "NUMBER OF TYPES" indicating that the number of bacterial types has changed. Note that, in the above case, each of the change information areas 516, 526, 536, and 546 of the chronological display screen 500 in FIG. 11 is also configured to show "NUMBER OF TYPES" so as to indicate that the number of bacterial types has changed.

In addition to the above, various modifications of the embodiment of the present invention may be made without departing from the scope of the technical idea defined by the claims.

What is claimed is:
1. A sample analyzer comprising:
   a light source for emitting light to particles contained in a measurement sample which is prepared from a reagent and a urine sample collected from a subject;

a detector for detecting scattered light and fluorescence which are generated from the particles in the measurement sample;
a display; and
a controller, wherein
the controller executes operations comprising:
obtaining particle data based on the scattered light and the fluorescence which are detected from the particles by the detector;
generating a scattergram in which pieces of the particle data are plotted based on the scattered light and the fluorescence;
setting a plurality of areas on the scattergram by dividing the scattergram at predetermined slope angles with respect to the origin of the scattergram;
determining the number of plots in each area of the scattergram;
creating a histogram which is generated based on the slope angles and the number of plots in each area of the scattergram;
controlling, when the histogram satisfies a first condition, the display to display first information indicating a possibility that the subject is infected with one type of bacteria; and
controlling, when the histogram satisfies a second condition, the display to display second information indicating a possibility that the subject is infected with two or more types of bacteria.

2. The sample analyzer of claim 1, wherein
predetermined areas each including the origin of the scattergram are excluded from the plurality of areas, respectively.

3. The sample analyzer of claim 1, wherein
the controller determines whether the histogram satisfies the first condition or the second condition based on the number of areas, among the plurality of areas, that comprise a greater number of plots than respective numbers of plots in areas adjacent thereto.

4. The sample analyzer of claim 1, wherein
the controller determines based on the shape of the histogram whether the histogram satisfies the first condition or the second condition.

5. The sample analyzer of claim 4, wherein
the controller determines based on the number of peaks shown in the histogram whether the histogram satisfies the first condition or the second condition.

6. The sample analyzer of claim 4, wherein
the controller determines based on the skewness of the histogram whether the histogram satisfies the first condition or the second condition.

7. The sample analyzer of claim 1, wherein
the controller controls the display to display the first information when the shape of the histogram satisfies the first condition, and controls the display to display the second information when the shape of the histogram satisfies the second condition.

8. The sample analyzer according to claim 7, wherein
the controller controls the display to display the first information when the number of peaks shown in the histogram satisfies the first condition, and controls the display to display the second information when the number of peaks shown in the histogram satisfies the second condition.

9. The sample analyzer according to claim 7, wherein
the controller controls the display to display the first information when the skewness of the histogram satisfies the first condition, and controls the display to display the second information when the skewness of the histogram satisfies the second condition.

10. A sample analyzer comprising:
a light source for emitting light to a measurement sample which is prepared from a reagent and a sample collected from a subject;
a detector for detecting scattered light and fluorescence which are generated from the measurement sample;
a memory;
a display; and
a controller, wherein
the controller executes operations comprising:
obtaining a measurement data based on the scattered light and the fluorescence;
generating a scattergram in which pieces of the measurement data are plotted based on the scattered light and the fluorescence;
setting a plurality of areas on the scattergram by dividing the scattergram at predetermined slope angles with respect to the origin of the scattergram;
determining the number of plots in each area of the scattergram;
creating a histogram which is generated based on the slope angles and the number of plots in each area of the scattergram;
determining a type of bacteria contained in the measurement sample based on an area of the scattergram corresponding to a peak of the histogram;
storing analysis result including the determined type of bacteria in the memory;
determining, based on analysis result of the subject that has most recently been obtained and analysis result of the subject that has previously been stored in the memory, whether a type of bacteria that the subject is suspected to be infected with has changed; and
controlling, when the type of bacteria has changed, the display to display information indicating that the type of bacteria has changed.

* * * * *